(12) United States Patent
Villoing et al.

(10) Patent No.: US 7,794,724 B2
(45) Date of Patent: Sep. 14, 2010

(54) FISH VACCINE

(75) Inventors: Stephane Villoing, Ulset (NO); Michel Bremont, Choisy le Roi (FR); Coralie Moriette, Paris (FR); Monique Le Berre, Montigny-le-Bretonneux (FR)

(73) Assignee: Intervet International B.V., Boxmeer (NL)

( * ) Notice: Subject to any disclaimer, the term of this patent is extended or adjusted under 35 U.S.C. 154(b) by 116 days.

(21) Appl. No.: 12/066,868

(22) PCT Filed: Sep. 15, 2006

(86) PCT No.: PCT/EP2006/066401

§ 371 (c)(1),
(2), (4) Date: Mar. 14, 2008

(87) PCT Pub. No.: WO2007/031572

PCT Pub. Date: Mar. 22, 2007

(65) Prior Publication Data

US 2009/0162388 A1    Jun. 25, 2009

(30) Foreign Application Priority Data

Sep. 16, 2005  (EP) .................................. 05020223

(51) Int. Cl.
*A61K 39/12* (2006.01)
(52) U.S. Cl. ................. 424/186.1; 424/204.1; 435/69.1
(58) Field of Classification Search ....................... None
See application file for complete search history.

(56) References Cited

U.S. PATENT DOCUMENTS 6,719,980 B1 *  4/2004  Weston et al. ............ 424/218.1

FOREIGN PATENT DOCUMENTS

WO      WO9958639      11/1999

OTHER PUBLICATIONS

E. Biering et al. Developments in Biologicals, 121:97-113. (2005).
P. Frost et al. Journal of General Virology, 76:1165-1172 (1995).
E.V. Agapov et al. Archives of Virology, 139:173-181 (1994).
C. Moriette et al. Journal of General Virology, 86:3119-3127 (2005).
G. Houghton, Diseases of Aquatic Organisms, 18:109-118 (1994).
K. Hodneland, et al. Diseases of Aquatic Organisms, 66:113-120 (2005).
H. Grosfeld, et al. Vaccine, 8:451-456 (1991).

* cited by examiner

*Primary Examiner*—Stacy B Chen
(74) *Attorney, Agent, or Firm*—William M. Blackstone; Aaron L. Schwartz

(57) ABSTRACT

The present invention relates to veterinary immunology, namely to the immunological response of fish to a virus. More specifically, the invention provides an epitope of salmonid alphaviruses which epitope is capable of inducing a virus neutralising immune response. In particular the invention relates to a polypeptide comprising a certain amino acid sequence, a protein comprising such polypeptide, to a carrier comprising such protein, and to a method of producing antibodies. Further the invention relates to a nucleic acid encoding such polypeptide or such protein, and to a carrier comprising such a nucleic acid. Also, the invention relates to a vaccine and a diagnostic kit comprising such a polypeptide, protein, carrier, or nucleic acid.

12 Claims, 8 Drawing Sheets

Figure 1:
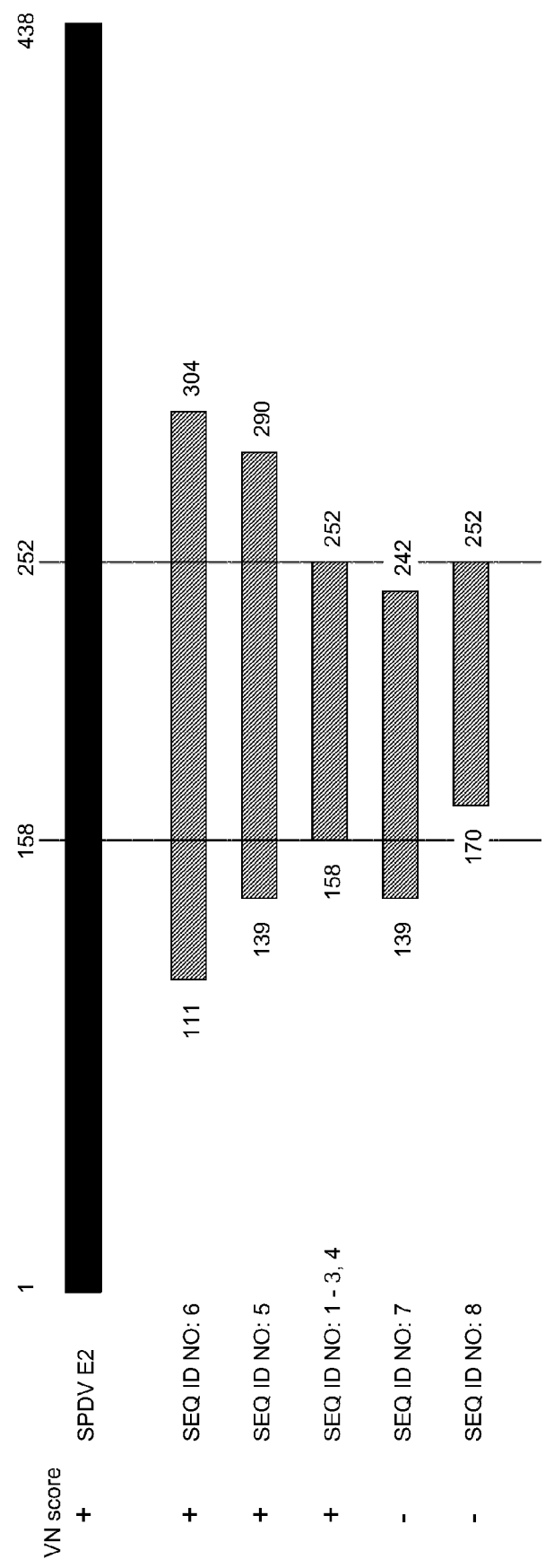

Figure 2:

```
                     158                                                                    207
          N3_ref     DLTKKCTRFS  TTPKKSAPYL  VDVYDALPIS  VEISTVVTCN  DNQCTVRVSP
       AAU01398.1    DLTKKCTRFS  TTPKKSAPYL  VDVYDALPIS  VEISTVVTCN  DNQCTVRVSP
       AAU01396.1    DLTKKCTRFS  TTPKKSAPYL  VDVYDALPIS  VEISTVVTCN  DNQCTVRVSP
       AAU01402.1    DLTKKCTRFS  TTPKKSAPYL  VDVYDALPIS  VEISTVVTCN  DNQCTVKVPP
      NP_740641.1    DMTKKCTRFS  TTPKKSALYL  VDVYDALPIS  VEISTVVTCS  DSQCTVRVPP
       CAB42823.1    DMTKKCTRFS  TTPKKSALYL  VDVYDALPIS  VEISTVVTCS  DSQCTVRVPP
       CAC87722.1    DMTKKCTRFS  TTPKKSALYL  VDVYDALPIS  VEISTVVTCS  DSQCTVRVPP
      NP_647497.1    DMTKKCTRFS  TTPKKSALYL  VDVYDALPIS  VEISTVVTCS  DSQCTVRVPP
       CAC87661.1    DLTKKCTRFS  TTPKKSALYL  VDVYDALPTS  VEISTVVTCN  ERQCTVRVPP
      NP_598185.1    DLTKKCTRFS  TTPKKSALYL  VDVYDALPTS  VEISTVVTCN  ERQCTVRVPP
      NP_740659.1    DLTKKCTRFS  TTPKKSALYL  VDVYDALPTS  VEISTVVTCN  ERQCTVRVPP
       CAB59730.1    DLTKKCTRFS  TTPKKSALYL  VDVYDALPTS  VEISTVVTCN  ERQCTVRVPP Consensus    DXTKKCTRFS  TTPKKSAXYL  VDVYDALPXS  VEISTVVTCX  XXQCTVXVXP
                     1                                                                      50

208                                                               252
          N3_ref     GTTVKFDKKC  KSAAQATVTF  TSDSQTFTCE  EPVLTAASIT  QGKPH
       AAU01398.1    GTTVKFDKKC  KSAAQATVTF  TSDSQTFTCE  EPVLTAASIT  QGKPH
       AAU01396.1    GTTVKFDKKC  KSAAQATVTF  TSDSQTFTCE  EPVLTAASIT  QGKPH
       AAU01402.1    GTTVKFDKKC  KSAAQATVTF  TSDSQTFTCE  EPVLTAASIT  QGKPH
      NP_740641.1    GTTVKFDKKC  KSADSATVTF  TSDSQTFTCE  EPVLTAASIT  QGKPH
       CAB42823.1    GTTVKFDKKC  KSADSATVTF  TSDSQTFTCE  EPVLTAASIT  QGKPH
       CAC87722.1    GTTVKFDKKC  KSADSATVTF  TSDSQTFTCE  EPVLTAASIT  QGKPH
      NP_647497.1    GTTVKFDKKC  KSADSATVTF  TSDSQTFTCE  EPVLTAASIT  QGKPH
       CAC87661.1    GTTVKFDKRC  KNAAKETVTF  TSDSQTFTCE  EPVLTAASIT  QGKPH
      NP_598185.1    GTTVKFDKRC  KNAAKETVTF  TSDSQTFTCE  EPVLTAASIT  QGKPH
      NP_740659.1    GTTVKFDKRC  KNAAKETVTF  TSDSQTFTCE  EPVLTAASIT  QGKPH
       CAB59730.1    GTTVKFDKRC  KNAAKETVTF  TSDSQTFTCE  EPVLTAASIT  QGKPH Consensus    GTTVKFDKXC  KXAXXXTVTF  TSDSQTFTCE  EPVLTAASIT  QGKPH
                     51                                                                 95
```

Figure 3

```
                   139                                                                        188
        N3_ref     EHQVTEKFTR ERSKGHHLSD LTKKCTRFST TPKKSAPYLV DVYDALPISV
     AAU01398.1    EHQVTEKFTR ERSKGHHLSD LTKKCTRFST TPKKSAPYLV DVYDALPISV
     AAU01396.1    EHQVTEKFTR ERSKGHHLSD LTKKCTRFST TPKKSAPYLV DVYDALPISV
     AAU01402.1    EHQVTEKFTR ERSKGHHLSD LTKKCTRFST TPKKSAPYLV DVYDALPISV
    NP_740641.1    EHQVTEKFTR ERSKGHHLSD MTKKCTRFST TPKKSALYLV DVYDALPISV
     CAB42823.1    EHQVTEKFTR ERSKGHHLSD MTKKCTRFST TPKKSALYLV DVYDALPISV
     CAC87722.1    EHQVTEKFTR ERSKGHHLSD MTKKCTRFST TPKKSALYLV DVYDALPISV
    NP_647497.1    EHQVTEKFTR ERSKGHHLSD MTKKCTRFST TPKKSALYLV DVYDALPISV
     CAC87661.1    EHQVTEKFTR ERSKGHHLSD LTKKCTRFST TPKKSALYLV DVYDALPTSV
    NP_598185.1    EHQVTEKFTR ERSKGHHLSD LTKKCTRFST TPKKSALYLV DVYDALPTSV
    NP_740659.1    EHQVTEKFTR ERSKGHHLSD LTKKCTRFST TPKKSALYLV DVYDALPTSV
     CAB59730.1    EHQVTEKFTR ERSKGHHLSD LTKKCTRFST TPKKSALYLV DVYDALPTSV Consensus    EHQVTEKFTR ERSKGHHLSD XTKKCTRFST TPKKSAlYLV DVYDALPXSV
                   1                                                                          50

189                                                                        238
        N3_ref     EISTVVTCND NQCTVRVSPG TTVKFDKKCK SAAQATVTFT SDSQTFTCEE
     AAU01398.1    EISTVVTCND NQCTVRVSPG TTVKFDKKCK SAAQATVTFT SDSQTFTCEE
     AAU01396.1    EISTVVTCND NQCTVRVSPG TTVKFDKKCK SAAQATVTFT SDSQTFTCEE
     AAU01402.1    EISTVVTCND NQCTVKVPPG TTVKFDKKCK SAAQATVTFT SDSQTFTCEE
    NP_740641.1    EISTVVTCSD SQCTVRVPPG TTVKFDKKCK SADSATVTFT SDSQTFTCEE
     CAB42823.1    EISTVVTCSD SQCTVRVPPG TTVKFDKKCK SADSATVTFT SDSQTFTCEE
     CAC87722.1    EISTVVTCSD SQCTVRVPPG TTVKFDKKCK SADSATVTFT SDSQTFTCEE
    NP_647497.1    EISTVVTCSD SQCTVRVPPG TTVKFDKKCK SADSATVTFT SDSQTFTCEE
     CAC87661.1    EISTVVTCNE RQCTVRVPPG TTVKFDKRCK NAAKETVTFT SDSQTFTCEE
    NP_598185.1    EISTVVTCNE RQCTVRVPPG TTVKFDKRCK NAAKETVTFT SDSQTFTCEE
    NP_740659.1    EISTVVTCNE RQCTVRVPPG TTVKFDKRCK NAAKETVTFT SDSQTFTCEE
     CAB59730.1    EISTVVTCNE RQCTVRVPPG TTVKFDKRCK NAAKETVTFT SDSQTFTCEE Consensus    EISTVVTCXX XQCTVXVXPG TTVKFDKXCK XAXXXTVTFT SDSQTFTCEE
                   51                                                                         100

239                                                                        288
        N3_ref     PVLTAASITQ GKPHLRSSML PSGGKEVKAR IPFPFPPETA TCRVSVAPLP
     AAU01398.1    PVLTAASITQ GKPHLRSSML PSGGKEVKAR IPFPFPPETA TCRVSVAPLP
     AAU01396.1    PVLTAASITQ GKPHLRSSML PSGGKEVKAR IPFPFPPETA TCRVSVAPLP
     AAU01402.1    PVLTAASITQ GKPHLRSSML PSGGKEVKAR IPFPFPPETA TCRVSVAPLP
    NP_740641.1    PVLTAASITQ GKPHLRSAML PSGGKEVKAR IPFPFPPETA TCRVSVAPLP
     CAB42823.1    PVLTAASITQ GKPHLRSAML PSGGKEVKAR IPFPFPPETA TCRVSVAPLP
     CAC87722.1    PVLTAASITQ GKPHLRSAML PSGGKEVKAR IPFPFPPETA TCRVSVAPLP
    NP_647497.1    PVLTAASITQ GKPHLRSAML PSGGKEVKAR IPFPFPPETA TCRVSVAPLP
     CAC87661.1    PVLTAASITQ GKPHLRSSML PSGGKEVKAR IPFPFPPETA TCRVSIAPLP
    NP_598185.1    PVLTAASITQ GKPHLRSSML PSGGKEVKAR IPFPFPPETA TCRVSIAPLP
    NP_740659.1    PVLTAASITQ GKPHLRSSML PSGGKEVKAR IPFPFPPETA TCRVSIAPLP
     CAB59730.1    PVLTAASITQ GKPHLRSSML PSGGKEVKAR IPFPFPPETA TCRVSIAPLP Consensus    PVLTAASITQ GKPHLRSXML PSGGKEVKAR IPFPFPPETA TCRVSXAPLP
                   101                                                                        150
```

Figure 3 (continued)

```
                        290
         N3_ref   SI
     AAU01398.1   SI
     AAU01396.1   SI
     AAU01402.1   SI
     NP_740641.1  SI
     CAB42823.1   SI
     CAC87722.1   SI
     NP_647497.1  SI
     CAC87661.1   SI
     NP_598185.1  SI
     NP_740659.1  SI
     CAB59730.1   SI Consensus  SI
                 152
```

Figure 4

```
                111                                                      160
       N3_ref   ILASCPEGQS ITVAATLDGT RHQCTTVFEH QVTEKFTRER SKGHHLSDLT
    AAU01398.1  ILASCPEGQS ITVAATLDGT RHQCTTVFEH QVTEKFTRER SKGHHLSDLT
    AAU01396.1  ILASCPEGQS ITVAATLDGT RHQCTTVFEH QVTEKFTRER SKGHHLSDLT
    AAU01402.1  ILASCPEGQS ITVAATLDGT RHQCTTVFEH QVTEKFTRER SKGHHLSDLT
    NP_740641.1 ILANCPVGQS LTVAATLDGT RHQCTTVFEH QVTEKFTRER SKGHHLSDMT
    CAB42823.1  ILANCPVGQS LTVAATLDGT RHQCTTVFEH QVTEKFTRER SKGHHLSDMT
    CAC87722.1  ILANCPVGQS LTVAATLDGT RHQCTTVFEH QVTEKFTRER SKGHHLSDMT
    NP_647497.1 ILANCPVGQS LTVAATLDGT RHQCTTVFEH QVTEKFTRER SKGHHLSDMT
    CAC87661.1  ILANCPVGQS LTVAATLDGT RHQCTTVFEH QVTEKFTRER SKGHHLSDLT
    NP_598185.1 ILANCPVGQS LTVAATLDGT RHQCTTVFEH QVTEKFTRER SKGHHLSDLT
    NP_740659.1 ILANCPVGQS LTVAATLDGT RHQCTTVFEH QVTEKFTRER SKGHHLSDLT
    CAB59730.1  ILANCPVGQS LTVAATLDGT RHQCTTVFEH QVTEKFTRER SKGHHLSDLT Consensus   ILAXCPXGQS XTVAATLDGT RHQCTTVFEH QVTEKFTRER SKGHHLSDXT
                1                                                         50

161                                                      210
       N3_ref   KKCTRFSTTP KKSAPYLVDV YDALPISVEI STVVTCNDNQ CTVRVSPGTT
    AAU01398.1  KKCTRFSTTP KKSAPYLVDV YDALPISVEI STVVTCNDNQ CTVRVSPGTT
    AAU01396.1  KKCTRFSTTP KKSAPYLVDV YDALPISVEI STVVTCNDNQ CTVRVSPGTT
    AAU01402.1  KKCTRFSTTP KKSAPYLVDV YDALPISVEI STVVTCNDNQ CTVKVPPGTT
    NP_740641.1 KKCTRFSTTP KKSALYLVDV YDALPISVEI STVVTCSDSQ CTVRVPPGTT
    CAB42823.1  KKCTRFSTTP KKSALYLVDV YDALPISVEI STVVTCSDSQ CTVRVPPGTT
    CAC87722.1  KKCTRFSTTP KKSALYLVDV YDALPISVEI STVVTCSDSQ CTVRVPPGTT
    NP_647497.1 KKCTRFSTTP KKSALYLVDV YDALPISVEI STVVTCSDSQ CTVRVPPGTT
    CAC87661.1  KKCTRFSTTP KKSALYLVDV YDALPTSVEI STVVTCNERQ CTVRVPPGTT
    NP_598185.1 KKCTRFSTTP KKSALYLVDV YDALPTSVEI STVVTCNERQ CTVRVPPGTT
    NP_740659.1 KKCTRFSTTP KKSALYLVDV YDALPTSVEI STVVTCNERQ CTVRVPPGTT
    CAB59730.1  KKCTRFSTTP KKSALYLVDV YDALPTSVEI STVVTCNERQ CTVRVPPGTT Consensus   KKCTRFSTTP KKSAXYLVDV YDALPXSVEI STVVTCXXXQ CTVRVXPGTT
                51                                                       100

211                                                      260
       N3_ref   VKFDKKCKSA AQATVTFTSD SQTFTCEEPV LTAASITQGK PHLRSSMLPS
    AAU01398.1  VKFDKKCKSA AQATVTFTSD SQTFTCEEPV LTAASITQGK PHLRSSMLPS
    AAU01396.1  VKFDKKCKSA AQATVTFTSD SQTFTCEEPV LTAASITQGK PHLRSSMLPS
    AAU01402.1  VKFDKKCKSA AQATVTFTSD SQTFTCEEPV LTAASITQGK PHLRSSMLPS
    NP_740641.1 VKFDKKCKSA DSATVTFTSD SQTFTCEEPV LTAASITQGK PHLRSAMLPS
    CAB42823.1  VKFDKKCKSA DSATVTFTSD SQTFTCEEPV LTAASITQGK PHLRSAMLPS
    CAC87722.1  VKFDKKCKSA DSATVTFTSD SQTFTCEEPV LTAASITQGK PHLRSAMLPS
    NP_647497.1 VKFDKKCKSA DSATVTFTSD SQTFTCEEPV LTAASITQGK PHLRSAMLPS
    CAC87661.1  VKFDKRCKNA AKETVTFTSD SQTFTCEEPV LTAASITQGK PHLRSSMLPS
    NP_598185.1 VKFDKRCKNA AKETVTFTSD SQTFTCEEPV LTAASITQGK PHLRSSMLPS
    NP_740659.1 VKFDKRCKNA AKETVTFTSD SQTFTCEEPV LTAASITQGK PHLRSSMLPS
    CAB59730.1  VKFDKRCKNA AKETVTFTSD SQTFTCEEPV LTAASITQGK PHLRSSMLPS Consensus   VKFDKXCKXA XXXTVTFTSD SQTFTCEEPV LTAASITQGK PHLRSXMLPS
                101                                                      150
```

Figure 4 (continued)

```
            261                                                    304
    N3_ref  GGKEVKARIP FPFPPETATC RVSVAPLPSI TYEESDVLLA GTAK
 AAU01398.1 GGKEVKARIP FPFPPETATC RVSVAPLPSI TYEESDVLLA GTAK
 AAU01396.1 GGKEVKARIP FPFPPETATC RVSVAPLPSI TYEESDVLLA GTAK
 AAU01402.1 GGKEVKARIP FPFPPETATC RVSVAPLPSI TYEESDVLLA GTAK
 NP_740641.1 GGKEVKARIP FPFPPETATC RVSVAPLPSI TYEESDVLLA GTAK
 CAB42823.1 GGKEVKARIP FPFPPETATC RVSVAPLPSI TYEESDVLLA GTAK
 CAC87722.1 GGKEVKARIP FPFPPETATC RVSVAPLPSI TYEESDVLLA GTAK
 NP_647497.1 GGKEVKARIP FPFPPETATC RVSVAPLPSI TYEESDVLLA GTAK
 CAC87661.1 GGKEVKARIP FPFPPETATC RVSIAPLPSI TYEESDVLLA GTAK
 NP_598185.1 GGKEVKARIP FPFPPETATC RVSIAPLPSI TYEESDVLLA GTAK
 NP_740659.1 GGKEVKARIP FPFPPETATC RVSIAPLPSI TYEESDVLLA GTAK
 CAB59730.1 GGKEVKARIP FPFPPETATC RVSIAPLPSI TYEESDVLLA GTAK Consensus GGKEVKARIP FPFPPETATC RVSXAPLPSI TYEESDVLLA GTAK
            151                                                    194
```

FISH VACCINE

CROSS REFERENCE TO RELATED APPLICATIONS

This application is a National Phase entry under 35 U.S.C. §371 of International Application No. PCT/EP2006/066401 filed Sep. 15, 2006 which claims priority to European Patent Application No: 05020223.3 EP filed Sep. 16, 2005.

REFERENCE TO SEQUENCE LISTING

The present invention relates to veterinary immunology, namely to the immunological response of fish to a virus. More specifically, the invention provides an epitope of salmonid alphaviruses which epitope is capable of inducing a virus neutralising immune response.

In particular the invention relates to a polypeptide comprising a certain amino acid sequence, a protein comprising such polypeptide, to a carrier comprising such protein, and to a method of producing antibodies. Further the invention relates to a nucleic acid encoding such polypeptide or such protein, and to a carrier comprising such a nucleic acid. Also, the invention relates to a vaccine and a diagnostic kit comprising such a polypeptide, protein, carrier, or nucleic acid.

The fish viruses salmon pancreas disease virus (SPDV) and sleeping disease virus (SDV) have been described to belong to the genus *alphavirus*, in the family Togaviridae (Villoing et al, 2000, J. of Virol., vol. 74, p. 173-183). The two aquatic viruses are closely related, and form a group that was found to be separate from the groups around the Sindbis-like and encephalitis-type alphaviruses (Powers et al, 2001, J. of Virol., vol. 75, p. 10118-10131). Therefore, they have been classified as variants of the species salmonid alphavirus (SAV) (Weston et al., 2002, J. of Virol., vol. 76, p. 6155-6163).

SDV has been isolated from trout in France and the United Kingdom (UK), and SPDV from salmon in Ireland and the UK. Also in trout and salmon from Norway, SPDV-like viruses have been isolated. Through genomic characterisation, these Norwegian isolates however were found to be a distinct subgroup. Therefore a subdivision of the SAV species has been proposed very recently (Weston et al, 2005, Dis. of Aq. Organ., vol. 66, p. 105-111; Hodneland et al, 2005, Dis. of Aq. Organ., vol. 66, p. 113-120), wherein SAV subtype 1 is formed by the viruses having resemblance to the SPDV isolates from Ireland and UK; subtype 2 is formed by the SDV isolates; and subtype 3 is formed by the Norwegian isolates of SPDV.

The three SAV subtypes are characterised by their reference strains:
- for subtype 1: SPDV isolate F93-125; the genomic sequence is available under GenBank accession number: AJ316244, and its envelope protein 2 (E2) as: CAC87722.
- for subtype 2: SDV isolate S49P; the genomic sequence is available under GenBank accession number: AJ316246, and its E2 protein as: CAB59730, amino acids 357-794.
- for subtype 3: SPDV isolate N3; the genomic sequence is available under GenBank accession number: AY604237, and its E2 protein as: AAU01400, amino acids 353-790.

The three SAV subtypes all cause a serious disease in salmon and trout, though the specific symptoms and their severity may vary with the subtype and the fish species. The various isolates are cross-protective to some extent, and antibodies to one of the subtypes show cross-reaction with the other subtypes.

A comprehensive overview of fish vaccines for aquaculture is from Sommerset et al., (2005, Expert Rev. Vaccines, vol. 4, p. 89-101). The aquaculture industry producing salmon or trout, suffers considerably from outbreaks of SAV, which cause reduced growth, and mortality of between 10-60 percent of the animals. Research has led to the development of vaccines (EP 712,926), and NORVAX® COMPACT PD., an inactivated SAV subtype 1 virus vaccine, is now available commercially for immunisation of salmon against SPDV. Vaccines based on SAV viral proteins have also been described (EP 1,075,523).

These described SAV vaccines although effective, however require careful selection of a process for the inactivation of the virus that does not diminish the viral immunogenicity. Also meticulous quality control of the viral inactivation process is required, to assure no live virus remains. The same is true for subunit vaccines based on whole proteins from a virus that are isolated from viral cultures. Consequently, production of such vaccines comes at a certain price.

An improvement is the production of subunit vaccines in a recombinant expression system, where no pathogenic virus is used. Nevertheless, the expression of the often large viral proteins is a heavy burden on the capacity of the expression system, making expression less effective. Also this is inefficient, as most of the protein expressed does not attribute to the actual immune-activation. On the contrary, many antigens possess immunodominant regions that are not involved in immuneprotection, but may even mask regions that are immuneprotective. As a result, immunisation with protein comprising such regions is counter-effective: an organism's humoral and/or cellular immunesystem is activated against these parts of the antigen but this does not interfere with the infection or the replication by the pathogen, or with the symptoms of disease.

Consequently there is a need for alternative SAV vaccines that are improved and more efficient, in that they are based on small but relevant immunogenic parts of the SAV viral proteins per se: the protective epitopes.

As is well known, the stimulation of an organism's immune system through T- and B-lymphocytes is based on the molecular recognition of an epitope by the T- or B-cell receptor. If epitopes are linear, they exist on an antigen as a continuous, sequential structure, and are relatively small; e.g. for protein, regions of 8-15 amino acids can be bound by MHC I or II molecules for presentation to the lymphocyte receptors (reviewed e.g. by Germain & Margulies, 1993, Annu. Rev. Immunol., vol. 11, p. 403-450). However, epitopes may also be formed as a result of the 3-dimensional folding of an antigen, such epitopes are discontinuous, and are assembled from e.g. amino acids that are not sequential in the protein's amino acid sequence. As a result, the region of an antigen spanning a discontinuous epitope is commonly larger than that of a linear epitope.

An epitope is protective if it can induce an immune response that is capable to effectively interfere with the extent or the progression of infection or disease.

Of all possible protective epitopes, either linear or conformational, those that cause virus neutralisation (VN) are most effective; such epitopes induce a humoral immune response that neutralises viral infectivity, and/or a cellular immune response that causes lysis of virus infected cells. Virus neutralisation is for instance effectuated by preventing viral attachment and/or entry into host cells.

Viral VN epitopes are commonly located on molecules involved in essential viral processes, such as for attachment or entry of host cells. Therefore their presence is relevant to the virus, leading to their conservation. This makes VN epitopes highly effective in vaccines, as well as in diagnostic assays.

The identification of an epitope in an antigen is a complex process, even though modern techniques can sometimes assist in their prediction: computer driven prediction can provide an indication of relevant areas. Such predictions use algorithms describing shape and charge of a protein, such as developed by Hopp & Woods (1981, Proc. Natl. Acad. Sci. USA, vol. 78, p. 3824-3828), and Chou & Fassman (1978, Advances in Enzymology, vol. 47, p. 45-148). However, such predictions are almost exclusively of use to linear epitopes. Computer prediction of discontinuous epitopes with some level of accuracy has been described (Kulkarni-Kale et at, 2005, Nucl. Acids Res., vol. 33, p. W168-W171), but this technique is only applicable to proteins of which the 3D crystal structure has been determined. Critical to all prediction methods is to follow up by verification whether the predicted epitope is at all immunogenic, and has protective capacity.

Similarly, the so-called Pepscan technique can be used to identify linear epitopes by an automated screening assay (Geysen et al., 1984, Proc. Natl. Acad. Sci. USA, vol. 81, p. 3998-4002). Again, this is of no use to discontinuous epitopes.

Mapping and characterisation of linear epitopes of alphaviruses has been described, e.g. for Semliki forest virus E2: the regions from amino acid (aa) 227-243, and 297-310 (Grosfeld et al, 1991, Vaccine, vol. 9, p. 451-456); regions 166-185, and 286-305 (Ariel, et al., 1990, Arch. Virol. vol. 113, p. 99-106); and region 297-352 (Grosfeld, et al., 1992, J. of Virol., vol. 66, p. 1084-1090).

Epitopes in alphaviral proteins that can induce a VN immune response have also been described: aa 170-220 of Sindbis virus E2 protein (Strauss & Strauss, 1994, Microbiol. Reviews, vol. 58, p. 491-562). Pence et al. (1990, Virology, vol. 175, p. 41-49), describe a discontinuous VN epitope of Sindbis virus E2 protein: E2c, covering the area of amino acids 62-159.

However, due to the low sequence homology between SAV and the other alphaviruses, none of these epitopes could be located on the SAV proteins. Homologies between structural protein sequences of SAV and other alphaviruses are in the order of 31-33% (Weston, 2002, supra).

For SAV itself, VN antibodies and their use in a serological assay have been described (Graham et al., 2003, J. of Fish Dis., vol. 26, p. 407-413), but these were polyclonal antibodies. Although effective in the assay described, such antibodies are not useful in the identification of a specific VN epitope, as such antibodies in an animal serum cover a wide variety of epitopes.

For this purpose of identifying VN epitopes on viral proteins, monoclonal antibodies are required. Although monoclonal antibodies against SAV proteins have been described (e.g. Graham et al, 2003, supra), these were not virus neutralising.

Consequently, so far no VN epitope of SAV viral proteins has been described. Nevertheless, for use in the fields of vaccination and diagnostics for SAV, it would be highly advantageous to have a VN epitope of an SAV viral protein.

It is therefore an object of the invention to provide for the first time a virus neutralising epitope from a salmonid alphavirus protein that allows for development of vaccines and diagnostics that improve on the efficacy and specificity of those known so far.

Surprisingly it was found now, that a polypeptide covering the amino acid region between aa 158 and 252 of the SAV E2 protein, incorporates a conformational, virus neutralising epitope of SAV E2 protein.

This VN epitope can now be employed for the generation of effective vaccines and diagnostic assays. The major advantage being that the VN epitope is very small in relation to the complete SAV E2 protein, which is 438 aa in size, while still incorporating the essential immunogenic portion of the SAV E2 protein.

This has a number of advantageous effects: the expression of the SAV E2 VN epitope in a recombinant expression system is much more efficient than that of the complete SAV E2, by not needlessly weighing on the capacity and the resources for expression of a bulk of protein that is not directly related to providing the essential immune response. In quantitative terms the efficiency of expression of the VN epitope over the full E2 is improved by 4.6 times (95 amino acids versus 438); additionally a qualitative improvement is reached: by not overloading the expression system's capacity for expression and post-translational processing, and therefore not inducing premature cell-lysis and subsequent proteolysis, the VN epitope protein produced is of better quality than the E2 protein would be.

Put in another way, when samples of SAV E2 VN epitope protein and of full length SAV E2 protein of the same amount are compared, then the immunogenic potency of the sample of VN epitope protein is more than 5 times higher than that of E2 protein. This is a surprising and highly relevant improvement of the efficiency of expression of SAV E2 subunits.

Another important advantage resulting from the small size of the SAV E2 VN epitope of the invention, is its improved possibility for being expressed by a live recombinant carrier (LRC); such LRC's, replicate in the vaccinated host, and often can only incorporate a limited amount of foreign nucleic acid into their genome. Advantageously, a nucleic acid encoding the VN epitope of the invention which measures less than 300 nucleotides, can be incorporated in most such live recombinant carriers, whereas a nucleic acid encoding the full length E2 protein, measuring over 1300 nucleotides, gives rise to problems in replication, transcription, and assembly and e.g. diminishes the replicative capacity of the LRC.

Alternatively, when an LRC does allow for larger foreign inserts, the small size of the SAV E2 VN epitope now allows for insertion of a number of inserts. Such multiple inserts can be inserted in fusion, that is, all behind one promoter, or each insert with its own promoter.

Improved efficiency of such an LRC is very relevant for vaccination in aquaculture: because of the animal husbandry methods employed, and the sheer number of animals to be vaccinated, individual handling of animals is impractical and very laborious. Therefore, the use of a self-replicating immunogen, such as an LRC which makes efficient mass-vaccination procedures possible, is an important efficiency improvement.

Therefore, in a first aspect, the invention relates to a polypeptide comprising an amino acid sequence having at least 90% amino acid identity to any one of SEQ ID NO: 1-3 in a region corresponding to said SEQ ID NO, characterised in that the polypeptide is at least 95 and at most 166 amino acids in size.

SEQ ID NO: 1-3 represent the aa region 158-252 of SAV E2 protein of the reference strains: F93-125, S49P, and N3 respectively.

For the invention expressions indicating an amino acid sequence region of the SAV E2 protein, such as 158-252 are to be interpreted to mean: starting with aa 158, up to and including aa 252.

By incorporating one of the sequences of SEQ ID NO: 1-3, the polypeptide of the invention comprises the region of amino acids 158-252 of SAV E2 protein, which region incorporates the discontinuous VN epitope of SAV E2 protein.

The length and position of the SEQ ID NO's described herein is presented graphically in FIG. 1, relative to the full length SAV E2.

For the invention, the term "polypeptide" is used only for clarity of reference, and is equal to "protein"; a "protein" is meant to incorporate a molecular chain of amino acids. A protein of itself is not of a specific length, structure or shape, and can if required, be modified in vivo or in vitro, by, e.g. glycosylation, amidation, carboxylation, phosphorylation, or changes in spatial folding. Also, protein-salts, -amides, and -esters (especially C-terminal esters), and N-acyl derivatives are within the scope of the invention. Inter alia, peptides, oligopeptides and polypeptides are included within the definition of protein, as well as precursor-, pre-pro- and mature forms of the protein. A protein can be of biologic and/or of synthetic origin. A protein may be a chimeric or fusion protein, created from fusion by biological, physical, or chemical processes, of two or more protein fragments.

The term "amino acid identity" refers to the degree of identity between the amino acid sequences of two or more proteins. The % amino acid identity of a protein with a protein according to the invention, must be determined by amino acid alignment of the region of that protein which corresponds to the amino acid sequence of any one of the SEQ ID NO: 1-3.

For the invention, such amino acid alignment must be determined with the computer program "BLAST 2 SEQUENCES" by selecting sub-program: "BlastP" (Tatusova & Madden, 1999, FEMS Microbiol. Letters, vol. 174, p. 247-2500). The comparison-matrix to be used is: "Blosum62", with the default parameters: open gap penalty: 11; extension gap penalty: 1, and gap x_dropoff: 50. This computer program reports the percentage of amino acids that are identical, that is counting only exact matches, as "Identities".

SAV E2 fragments containing this region of aa 158-252 of SAV E2, were found to contain the VN epitope of the invention. This is evident from the experimental results obtained; the positive VN scores are also indicated in FIG. 1, and these and other results are outlined in the experimental section.

It was found now that upon multiple alignment of the amino acid region 158-252 from many SAV E2 proteins, comprising isolates from each of the three SAV subtypes, the level of amino acid identity found varied between 90 and 100%. This is represented in Table 1 below, and in FIG. 2. This very high level of conservation indicates that variations in amino acid sequence identity of 90%, are within the natural variation of the amino acid sequences that are found in this region of the E2 protein of SAV. Therefore proteins having amino acid identities within this range of 90-100% to polypeptides according to the invention, apparently are natural variants and therefore are within the scope of the invention.

TABLE 1

Percentage amino acid identity of amino acid regions 158-252 from SAV E2 proteins compared to one reference sequence:

| Access. nr. | % aa identity to reference | SAV type | SAV isolate | SEQ ID NO: |
|---|---|---|---|---|
| AAU01400.1 | reference | 3 | N3 | 3 |
| AAU01398.1 | 100 | 3 | CMS1 | |
| AAU01396.1 | 100 | 3 | Hav1 | |
| AAU01402.1 | 97 | 3 | Tun1 | |
| NP_740641.1 | 92 | 1 | | |
| NP_647497.1 | 92 | 1 | | |
| CAC87722.1 | 92 | 1 | F93-125 | 1 |
| CAB42823.1 | 92 | 1 | | |
| CAC87661.1 | 90 | 2 | | |
| NP_598185.1 | 90 | 2 | S49P | 2 |
| CAB59730.1 | 90 | 2 | | |
| NP_740659.1 | 90 | 2 | | |

Results were determined using the ALIGN+® PROGRAM (SE Central), with settings to "global alignment against a reference sequence", using exact matches, a scoring matrix = Blosum 62, and other parameters set at default value. The reference sequence was that of SAV isolate N3 (acc. nr: AAU01400.1)

In a preferred embodiment, the polypeptide according to this aspect of the invention comprises an amino acid sequence having at least 91% amino acid sequence identity to any one of SEQ ID NO: 1-3. More preferred is a polypeptide having 92, 93, 94, 95, 96, 97, 98, 99, or even 100% amino acid sequence identity to any one of SEQ ID NO: 1-3, in that order of preference.

Preferably the size for a polypeptide according to this aspect of the invention does not exceed 166 amino acids. This corresponds to the length of the region from aa 139-304 of SAV E2 protein.

As a result, polypeptides according to this aspect of the invention may be derived from the SAV E2 protein from anywhere between aa 87 (being position 252 minus 166) and aa 323 (being position 158 plus 166), provided they have a maximum length of 166 amino acids. Such polypeptides still incorporate an amino acid sequence region corresponding to the SAV E2 region of aa 158-252 which contains the VN epitope according to the invention, and because of the natural variation that exists in SAV E2 sequences in this region, their percentage of amino acid identity to SEQ ID NO: 1-3 is between 90 and 100%.

Techniques to obtain the polypeptides according to the invention are well known in the art. Preferably genetic engineering techniques and recombinant DNA expression systems are employed to express exactly the desired fragments.

The nucleic acid sequences that can be used to encode a polypeptide according to the invention are described herein and/or are publicly available. Such sequences can be obtained, manipulated and expressed by standard molecular biology techniques that are well-known to the skilled artisan, and that are explained in great detail in standard text-books like: Molecular cloning: a laboratory manual (Sambrook & Russell: 2000, Cold Spring Harbor Laboratory Press; ISBN: 0879695773), and: Current protocols in molecular biology (Ausubel et al., 1988+updates, Greene Publishing Assoc., New York; ISBN: 0471625949).

To construct a nucleic acid encoding a polypeptide according to the invention, preferably DNA fragments in the form of plasmids are employed. Such plasmids are useful e.g. for enhancing the amount of a DNA-insert, for use as a probe, and as tool for further manipulations. Examples of such plasmids for cloning are plasmids of the pET, pBRp, pUC, pGEM, and pcDNA plasmid series, all these are readily available from several commercial suppliers.

To obtain the desired polypeptide, the proper nucleic acid sequences are constructed e.g. by using restriction enzyme digestion, by site directed mutations, or preferably by polymerase chain reaction (PCR) techniques. Standard techniques and protocols for performing PCR are for instance extensively described in: PCR primers: a laboratory manual (Dieffenbach & Dveksler, 1995, CSHL Press, ISBN 879694473). For instance, by selecting a PCR primer that hybridises at a particular place on an SAV E2 encoding gene, rec DNA fragments are produced that encode polypeptides starting or ending at the desired amino acid of the SAV E2.

For the purpose of cloning, protein purification, detection, or improvement of expression level, additional sequences may be added, preferably already incorporated in the PCR-primers used.

The DNA encoding the polypeptide according to the invention can e.g. be cloned from the PCR product into an expression vector. In such expression vectors, the nucleic acid encoding the desired fragment of SAV E2 is operably linked to a transcriptional regulatory sequence such that it is capable of controlling the transcription of the nucleic acid sequence. Suitable expression vectors are, amongst others, plasmids, cosmids, viruses and YAC's (Yeast Artificial Chromosomes) which comprise the necessary control regions for replication and expression.

Transcriptional regulatory sequences are well-known in the art and comprise i.a. promoters and enhancers. Those skilled in the art are well aware that the choice of a promoter extends to any eukaryotic, prokaryotic or viral promoter capable of directing gene transcription, provided that the promoter is functional in the expression system that is to be used.

Transcriptional regulatory sequences that are suitable for use in an expression DNA plasmid comprise promoters such as the (human) cytomegalovirus immediate early promoter and the Rous sarcoma virus LTR promoter (Ulmer et al., 1993, Science, vol. 259, p. 1745-1748), and the major late promoter of Adenovirus 2 and the β-actin promoter (Tang et al, 1992, Nature, vol. 356, p. 152-154). The regulatory sequences may also include terminator and polyadenylation sequences, such as the well known bovine growth hormone polyadenylation sequence, the SV40 polyadenylation sequence, and the human cytomegalovirus terminator and polyadenylation sequences.

Bacterial, yeast, fungal, insect, and vertebrate cell expression systems are used very frequently. Such expression systems are well-known in the art and generally available, e.g. through Invitrogen (the Netherlands).

A host cell used for expression of a polypeptide or protein (as outlined below) according to the invention, may be a cell of bacterial origin, e.g. from *Escherichia coli, Bacillus subtilis, Lactobacillus* sp., or *Caulobacter crescentus*, or the aquatic bacteria *Yersinia ruckeri*; and *Vibrio anguillarum*, all in combination with the use of bacteria-derived plasmids or bacteriophages for expressing the sequence encoding the polypeptide or protein (as outlined below) according to the invention. The host cell may also be of eukaryotic origin, e.g. yeast-cells (e.g. *Saccharomyces* or *Pichia*) in combination with yeast-specific vector molecules; insect cells in combination with recombinant baculo-viral vectors e.g. Sf9 and pVL1393 (Luckow et al., 1988, Bio-technology, vol. 6, p. 47-55); plant cells, in combination with e.g. Ti-plasmid based vectors or plant viral vectors (Barton, et al., 1983, Cell, vol. 32, p. 1033-1043); or mammalian cells also with appropriate vectors or recombinant viruses, such as Hela cells, CHO, CRFK, or BHK cells, or fish cells such as Chinook salmon embryo (CHSE-214) cells, Atlantic salmon cell lines and Rainbow trout cell lines.

Next to these expression systems, expression in organisms such as algae, or plants, are attractive expression systems, as these can be incorporated into the feed, and be used as oral vaccine. By feeding such materials to fish to be vaccinated, efficient mass vaccination is achieved.

The technique of in vivo homologous recombination, well-known in the art, can be used to introduce a recombinant nucleic acid sequence into the genome of a bacterium, virus, or organism of choice.

Expression may also be performed in so-called cell-free expression systems. Such systems comprise all essential factors for expression of an appropriate recombinant nucleic acid, operably linked to a promoter that is capable of expression in that particular system. Examples are the *E. coli* lysate system (Roche, Basel, Switzerland), or the rabbit reticulocyte lysate system (Promega corp., Madison, USA).

In an other embodiment, the invention relates to a protein comprising the polypeptide of the invention, whereby said protein does not comprise a part of an SAV E2 protein comprising said polypeptide and being more than 166 amino acids in size.

Such proteins according to the invention are fusion- and carrier proteins comprising the polypeptide according to the invention.

A fusion or carrier protein is formed through an assembly of two or more strands of amino acids, giving a combination that does not occur naturally. The strands can be of equal or different length. The combination of the strands can be accomplished by several means, e.g.:

- chemically; by coupling, conjugation or cross-linking, through dehydration, esterification, etc., of the amino acid sequences either directly or through an intermediate structure.
- physically; by coupling through capture in or on a macromolecular structure
- by molecular-biological fusion; through the combination of recombinant nucleic acid molecules which comprise fragments of nucleic acid capable of encoding each of the two, such that a single continuous expression product is finally produced.

Techniques for applying these couplings and fusions are well known in the art, and are for instance described in the handbooks of Sambrook & Russel, and of Ausubel, as described supra.

The use of such fusion- or carrier-proteins has several advantages, for instance:

- easier handling; for example in purification, and detection,
- increased immunogenicity; for example by general immunostimulation comparable to an adjuvant, or by specific manipulation of the immunesystem in a certain direction (e.g. Th1 or Th2), to a certain level of response (higher or lower than otherwise), or to obtain a certain timing of the immune response.
- increased expression level; for instance by enhancing the level of the expression per se, e.g. by enhancing transcription or translation levels in a particular expression system, or by improving the stability of the produced mRNA, or of the protein, either intra- or extracellularly.

providing a linker or spacer region for yet another fusion or carrier protein, etc.

Examples of such carrier or fusion proteins are well known, for instance:
   for purification or detection: His-tag, v-Myc-tag, β-galactosidase (β-gal), maltose binding protein, green fluorescent protein (GFP), gluthation S-transferase, streptavidin, biotin, immunoglobulin derived domains (e.g. Fab-fragments), etc.
   for improved or adapted immune response: bovine or ovine serum albumin, keyhole limpet haemocyanin, hsp70, tetanus toxoid, and: interleukins, cytokines, and hormones that are biologically active in salmonid fish.

Several of these examples have more than a single effect, for instance by attaching GFP, both detection and expression is improved.

In an alternative aspect, the invention relates to a polypeptide comprising a part of an SAV E2 protein, characterised in that said part has at least the amino acid sequence of SEQ ID NO: 4 and at most the amino acid sequence of SEQ ID NO: 6.

SEQ ID NO: 4 is the consensus sequence derived from the multiple alignment of the fragments aa 158-252 from SAV E2 proteins, already described above in Table 1. The alignment and the consensus sequence are depicted in FIG. 2.

SEQ ID NO: 5 and 6 are consensus sequences derived in a similar way from SAV E2 proteins, covering aa 139-290, and 111-304 respectively. The underlying multiple alignments are depicted in FIGS. 3, and 4 respectively.

Such a polypeptide according to the invention, comprises a part of the SAV E2 protein that is equal or larger than SEQ ID NO: 4, but not larger than SEQ ID NO: 6. Such polypeptides still comprise the discontinuous VN epitope of SAV E2 protein, through the incorporation of SEQ ID NO: 4.

Polypeptides according to the invention, have a size of between 95 and 194 amino acids (respectively the length of SEQ ID NO: 4 and 6), and are selected from the sequence of this region of SAV E2.

Because SEQ ID NO: 4 and 6 are consensus sequences, a certain level of variability in the amino acid sequence of the polypeptides according to this aspect of the invention is within the scope of the invention. These consensus sequences have at least 85% amino acid identity to the region of aa 158-252 of any of the three SAV subtypes.

One example of a protein according to this aspect of the invention is SEQ ID NO: 5, which runs from aa 139-290 relative to the sequence of SAV E2.

In a preferred embodiment, the polypeptide according to this aspect of the invention, comprises SEQ ID NO: 4, with an increased level of amino acid sequence identity, obtained by replacing one or more of the variable amino acids (indicated by the symbol X or Xaa, representing any amino acid) at a certain position in SEQ ID NO: 4, corresponding to a certain position in the SAV E2, by one of the amino acids indicated for that position in Table 2:

TABLE 2

Preferred embodiments of SEQ ID NO: 4; amino acids to replace the variable amino acids in SEQ ID NO: 4.

| position in SEQ ID NO: 4 | position in SAV E2 | replace X by: |
|---|---|---|
| 2 | 159 | L or M |
| 18 | 177 | P or L |

TABLE 2-continued

Preferred embodiments of SEQ ID NO: 4; amino acids to replace the variable amino acids in SEQ ID NO: 4.

| position in SEQ ID NO: 4 | position in SAV E2 | replace X by: |
|---|---|---|
| 29 | 186 | I or T |
| 40 | 197 | N or S |
| 41 | 198 | D or E |
| 42 | 199 | N, S, or R |
| 47 | 204 | R or K |
| 49 | 206 | S or P |
| 59 | 216 | K or R |
| 62 | 219 | S or N |
| 64 | 221 | A or D |
| 65 | 222 | Q, S, or K |
| 66 | 223 | A or E |

A similar table can be set up for each of SEQ ID NO: 5 or 6, by deriving the preferred amino acids from the multiple alignments of FIG. 3 or 4, respectively.

For both alternatives of the polypeptide of the invention applies that the exact borders of the VN epitope of SAV E2 can be further defined by the skilled person based on the information provided herein, by using well known techniques. The current borders indicated according to the invention, are set at aa 158-252, whereas it was found that fragments from aa 139-242 (SEQ ID NO: 7, from SAV subtype 3, isolate N3), and from aa 170-252 (SEQ ID NO: 8, from SAV subtype 3, isolate N3) both do not possess a functional VN epitope. Consequently the borders of the strictest region comprising the VN epitope are, on the N-terminal side: between aa 158 and 170, and on the C-terminal side: between 242 and 252.

In an embodiment of the polypeptide of this aspect of the invention, the invention relates to a protein comprising the polypeptide of the invention, whereby said protein does not comprise a part of an SAV E2 protein comprising said polypeptide and being larger in size than said polypeptide.

Similar to the advantageous uses of the protein of the alternative aspect of the invention, these proteins now provide fusion- or carrier-proteins comprising the VN epitope of SAV E2 protein that allow for instance: easier handling, increased immunogenicity, or an increased expression level of the VN epitope of the invention.

Techniques to produce such fusion- or carrier proteins, as described before, are well known in the art.

In another aspect, the invention relates to a carrier comprising a protein according to the invention.

Such carriers according to this aspect of the invention are organic or anorganic (multi-) molecular structures that can advantageously be employed for instance to improve the stability, the immunogenicity, the delivery, or the utility as a diagnostic, of the protein according to the invention. Examples of carrier molecules of use to vaccination and immunostimulation are: proteins, lipids, carbohydrates; vesicles such as micelles, liposomes, ISCOM's, dendromers, niosomes, blo-microcapsules, micro-alginates, macrosols; anorganic compounds such as aluminium-hydroxide, -phosphate, -sulphate or -oxide, silica, Kaolin®, and Bentonite®; and host cells and live recombinant carriers.

Carriers, of use for diagnostic purposes comprise for example particles of silica, latex, or gold; membranes of nylon, PVDF, nitrocellulose, or paper; and objects such a silicium chip or a micro-titration devices.

Techniques for the incorporation, coupling, and attachment of a protein according to the invention to such carriers are well known in the art. All such embodiments are described in more detail below.

Embodiments of carrier proteins, comprise much the same examples as described above, now providing for instance: easier handling, increased immunogenicity, or an increased expression level of the proteins comprising a polypeptide according to the invention.

Carbohydrates and lipids as carrier for a protein according to the invention, are for instance lectins, glucans, glycans and lipopolysaccharides, such as lipid A. Techniques for coupling of a protein according to the invention with such molecules are well known in the art (e.g. Kubler et al., 2005, J. Org. Chem., vol. 70, p. 6987-6990; Alving, 1991, J. Immunol. Methods, vol. 140, p. 1-13).

Carrier vesicles serve multiple purposes, for instance as stabiliser, as delivery vehicle and as immunostimulant. For instance ISCOM's are well known immunostimulating particles (WO 96/11711), consisting of a mixture of saponin, a phospholipid and cholesterol, into which an antigen such as a protein according to the invention can be incorporated. Alternatively, Iscom-matrix particles can be produced. These are Iscom-like particles in which the subunit antigen is not integrated but adsorbed.

Carriers for use in oral vaccination, provide both delivery and immune stimulation. Examples are metabolisable substances such as alpha-cellulose or different oils of vegetable or animal origin. Also an attractive way is the use of live feed organisms as carriers; when such organisms have taken up or adsorbed the protein according to the invention, they can be fed to the target fish. Particularly preferred feed carriers for oral delivery of the protein according to the invention are live-feed organisms which are able to encapsulate the protein. Suitable live-feed organisms include plankton-like non-selective filter feeders, preferably members of *Rotifera, Artemia*, and the like. Highly preferred is the brine shrimp *Artemia* sp.

A preferred method of preparing a feed carrier is to feed host cells or cells from an expression system, comprising the protein according to the invention, to plankton-like non-selective filter feeders preferably members of *Rotifera, Artemia*, and the like. The protein is taken up by the live feed carrier such as plankton-like non-selective filter feeders, and the invention. Such an LRC is then administered to target fish for instance by immersion vaccination.

A host cell comprising a polypeptide, protein, nucleic acid, or LRC according to the invention, can also be used as carrier. For instance the cells of the expression system that was used to produce the polypeptide or protein according to the invention, or the cells used to produce an LRC according to the invention may be formulated into a pharmaceutical composition, such as a vaccine, and be administered to the target fish. As with LRC's, antigens from the host cell will provide some additional immunostimulation, having an adjuvating effect.

Anorganic carriers can be coated with, or can adsorb a peptide or protein according to the invention using well known techniques. Such loaded carriers are then employed in vaccine formulations for application to target fish, or for application in diagnostic assays. For instance aluminium hydroxide is a well known vaccine adjuvant. Similarly, particles of silica (glass beads) or gold are commonly used in diagnostic assays.

Carriers comprising a polypeptide or protein according to the invention can also be used in diagnostic assays. For instance membranes or strips of a suitable material, such as nylon, PVDF, nitrocellulose, or paper can be produced by adsorbing, coating, or blotting the polypeptide or protein according to the invention. Techniques for e.g. blotting using a liquid flow or electric current are well known in the art. Such membranes are then incorporated in a test device or diagnostic kit. Objects may also serve as carrier: for instance a silicium chip for use in BIAcore equipment, or a micro-titration device with wells coated with the polypeptide or the protein according to the invention, can advantageously be used.

A diagnostic assay using such a carrier is very favourable for the specific detection of SAV. In particular because the VN epitope of SAV E2 comprised in a polypeptide, protein, or carrier according to the invention allows specific detection of al three subtypes of SAV; as described herein, the VN epitope of SAV E2 is much conserved between the three subtypes, having amino acid identities between 90 and 100%.

Such specific identification of SAV is for instance very useful in the determination of the cause of disease; e.g. the aquatic Birnavirus infectious pancreatic necrosis virus (IPNV) also causes disease and mortality in salmonid fish. As the symptoms of SPDV and IPNV can be difficult to differentiate, having a sensitive and specific diagnostic test for SAV available greatly improves the possibilities for applying the correct measures to the animal husbandry and health care.

It is one of the merits of the invention that the polypeptide, protein, or carrier according to the invention, can also be used to produce specific antibodies against the SAV E2 VN epitope. As a result, it is now for the first time possible to produce antibodies, monoclonal or polyclonal, that are almost exclusively directed against the SAV E2 VN epitope. Such antibodies are highly specific for SAV, and highly effective in for instance passive immunisations and diagnostic assays (as will be outlined below). Such antibodies are then used e.g. for therapy, for diagnostics, or for quality assurance purposes.

Therefore in an embodiment the invention relates to a method of producing salmonid alphavirus neutralising antibodies, comprising the inoculation of the polypeptide, the protein, or the carrier according to the invention into an animal, and isolation of antibodies.

Methods of raising and producing antibodies, or antisera comprising antibodies, as well as the concept of "specific binding" by an antibody, are well-known in the art. For instance antibodies or antiserum against the polypeptide, the protein, or the carrier according to the invention can be obtained quickly and easily by vaccination of e.g. pigs, poultry or rabbits with the polypeptide, protein, or carrier according to the invention in e.g. a water-in-oil emulsion followed, after 2-6 weeks, by bleeding, centrifugation of the coagulated blood and decanting of the sera.

Another source of antibodies is the blood or serum of trout or salmon that have been (naturally) infected with SAV.

Other methods for the preparation of antibodies, which may be polyclonal, monospecific, or monoclonal (or derivatives thereof) are well-known in the art. If polyclonal antibodies are desired, techniques for producing and processing polyclonal sera are well-known in the art (e.g. Mayer and Walter eds., 1987, Immunochemical Methods in Cell and Molecular Biology, Academic Press, London).

Monoclonal antibodies, reactive against the polypeptide or protein according to the invention can be prepared by immunizing inbred mice by techniques also known in the art (Kohler & Milstein, 1975, Nature, vol. 256, p. 495-497).

In a further aspect, the invention relates to a nucleic acid encoding the polypeptide or the protein according to the invention.

The term "nucleic acid" is meant to incorporate a molecular chain of desoxy- or ribo-nucleic acids. A nucleic acid is not of a specific length, therefore polynucleotides, genes, open reading frames (ORF's), probes, primers, linkers, spacers and adaptors, consisting of DNA and/or RNA, are included within the definition of nucleic acid. A nucleic acid can be of biologic and/or synthetic origin. The nucleic acid may be in single stranded or double stranded form. The single strand may be in sense or anti-sense orientation. Modifications in the bases of the nucleic acid may be made, and bases such as Inosine may be incorporated. Other modifications may involve, for example, modifications of the backbone.

With the term "encoding" is meant: providing the possibility of protein expression, i.a. through transcription and/or translation when brought into the right context. The right context refers to the promoter, cells, buffer, reaction conditions, etc.

A nucleic acid according to the invention when brought into the right context, is capable of encoding a polypeptide or a protein according to the invention. Examples of nucleic acids according to the invention have been described above. Methods to isolate a nucleic acid capable of encoding a polypeptide or protein according to the invention have been described above and are well-known in the art. For instance the SAV E2 VN epitope contained in polypeptides as depicted in SEQ ID NO: 1-3 can be used to make or isolate probes or primers. These are then used to screen libraries of genomic or mRNA sequences by PCR or hybridization selection. From a positive clone or colony, the VN epitope containing fragment is then isolated, sub cloned and used e.g. in an expression system.

Alternatively, E2 VN epitopes according to the invention, from other SAV isolates can now conveniently be identified by computerised comparisons of SEQ ID NO:1-3 in silico to other SAV sequences that may be comprised in a computer database. For that purpose many computer programs are publicly available. For instance the suite of BLAST programs (Altschul et al, 1997, Nucleic Acids Res., vol. 25, p. 3389-3402) can be employed to compare SEQ ID NO: 1-3 to expressed sequence tags (EST)- and genomic sequence databases.

Nucleic acids according to the invention also include nucleic acids having variations in the nucleotide sequence when compared to SEQ ID NO: 1-6 "Variant" nucleic acids may be natural or non-natural variants. Natural variants exist in the various isolates of SAV; non-naturally occurring variants may be created by rec DNA techniques.

It is well-known in the art, that many different nucleic acids can encode one and the same protein. This is a result of what is known in molecular biology as "wobble", or the "degeneracy of the genetic code", wherein several different codons or triplets of mRNA will cause the same amino acid to be attached to the chain of amino acids growing in the ribosome during translation. It is most prevalent in the second and especially the third base of each triplet encoding an amino acid. This phenomenon can result in a heterology of about 30% for two different nucleic acids that still encode the same protein. Thus, two nucleic acids having a nucleotide sequence identity of about 70% can still encode one and the same protein.

Nucleic acids encoding a polypeptide or protein according to the invention, can be obtained, manipulated and expressed by standard techniques in molecular biology, as described above. The tools for such manipulations and expressions are carriers for the nucleic acid according to the invention.

Therefore a further aspect of the invention relates to a carrier comprising a nucleic acid according to the invention, whereby said carrier is selected from the group consisting of a DNA fragment, a recombinant DNA molecule, a live recombinant carrier, and a host cell. These are described in more detail below.

In a preferred embodiment the invention relates to a DNA fragment comprising a nucleic acid according to the invention.

A preferred carrier is a DNA plasmid.

The preferred method of obtaining a DNA fragment is by reverse transcription of isolated mRNA by using RT-PCR. PCR techniques are commonly known, as described above.

An isolated cDNA sequence may be incomplete due to incomplete transcription from the corresponding mRNA, or clones may be obtained containing fragments of the complete cDNA. Various techniques are known in the art to complete such partial cDNA sequences, such as RACE (rapid amplification of cDNA ends).

In another preferred embodiment the invention relates to a recombinant DNA molecule comprising a nucleic acid, or a DNA fragment according to the invention, wherein the nucleic acid, or the DNA fragment are functionally linked to a promoter.

To construct a recombinant DNA molecule according to the invention, DNA plasmids carrying promoters can advantageously be employed, as described above.

In yet another preferred embodiment, the invention relates to a live recombinant carrier (LRC) comprising a nucleic acid, a DNA fragment, or a recombinant DNA molecule according to the invention. LRC's have been described in detail above.

The DNA fragment, the recombinant DNA molecule, or the LRC according to the invention may additionally comprise other nucleotide sequences such as immune-stimulating oligonucleotides having unmethylated CpG dinucleotides, or nucleotide sequences that code for other antigenic protein, or adjuvating cytokines.

In still another preferred embodiment, the invention relates to a host cell comprising a nucleic acid, a DNA fragment, a recombinant DNA molecule, or an LRC, all according to the invention.

A host cell according to the invention may comprise such a nucleic acid, DNA fragment, recombinant DNA molecule, or LRC according to the invention, stably integrated into its genome, or on an extrachromosomal body replicating autonomously.

Examples of host cells as carrier, or for the purpose of expression of a polypeptide or protein according to the invention have been described above. In the use as a vaccine, the host cell may be live or inactivated, depending on the desired effect. Many physical and chemical methods of inactivation of cells are known in the art; examples of physical inactivation are by heating, or by radiation, e.g. with UV, X-rays or gamma-radiation. Examples of inactivating chemicals are β-propiolactone, glutaraldehyde, β-ethylene-imine and formaldehyde. When a method of inactivation is to be applied, the skilled person knows this requires optimisation, in order not to disturb the immunogenicity of the polypeptide, protein, carrier, or nucleic acid that is to be delivered, comprised in the host cell, to the target animal.

Preferred use of a nucleic acid, a DNA fragment, a recombinant DNA molecule, an LRC, or a host cell according to the invention is in expression and delivery of the SAV E2 VN epitope. One way to achieve that is through DNA vaccination. DNA plasmids carrying a nucleic acid, a DNA fragment, a recombinant DNA molecule according to the invention can be administered to a salmonid fish as described above. Such methods are well-known in the art.

Nucleic acid vaccines (or gene- or genetic-vaccines as they are called) may require a targeting- or a delivery vehicle other than an LRC to target or protect it, or to assist in its uptake by (the cells of) the host. Such vehicles may be biologic or synthetic, and are for instance bacteriophages, virus-like particles, liposomes, or micro-, powder-, or nano particles.

DNA vaccines can easily be administered through intradermal application e.g. using a needle-less injector such as a GENEGUN®. This way of administration delivers the DNA directly into the cells of the animal to be vaccinated. A preferred amount of a nucleic acid, a DNA fragment, or a recombinant DNA molecule according to the invention, comprised in a pharmaceutical composition according to the invention (as outlined below) is in the range between 10 pg and 1000 µg. Preferably, amounts in the range between 0.1 and 100 µg are used. Alternatively, fish can be immersed in solutions comprising e.g. between 10 pg and 1000 µg/ml of the DNA to be administered. All these are well-known in the art.

Similarly, a targeting- or delivery vehicle comprising a nucleic acid, a DNA fragment, or a recombinant DNA molecule according to the invention, is within the scope of a carrier according to the invention.

These uses will result in nucleic acid being delivered, or protein being expressed inside the target organism or its cells.

The medical uses of a polypeptide, protein, carrier, or nucleic acid according to the invention have been described above. In essence this is the vaccination of fish against SAV, in order to prevent or ameliorate, infection or disease, by interfering with the establishment and/or with the progression of an SAV infection, or with the progression of clinical symptoms of SAV induced disease.

These medical uses are put to practice in aquatic animal health care e.g. by administering to a salmonid fish a polypeptide, protein, carrier, or nucleic acid according to the invention.

Therefore, another aspect of the invention relates to a pharmaceutical composition comprising the polypeptide, protein, carrier, or nucleic acid according to the invention, and a pharmaceutically acceptable carrier.

In an embodiment, the pharmaceutical composition of the invention relates to a vaccine comprising a polypeptide, a protein, a carrier, or a nucleic acid according to the invention, and a pharmaceutically acceptable carrier.

In a further aspect, the invention relates to the polypeptide, protein, carrier, or nucleic acid according to the invention, for use as a medicament for fish.

In a further aspect, the invention relates to the use of a polypeptide, protein, carrier, or nucleic acid according to the invention, for the manufacture of a medicament for fish.

In a further aspect, the invention relates to a method of vaccination of fish by administering to such organism a polypeptide, protein, carrier, or nucleic acid according to the invention, in a pharmaceutically effective amount and in a pharmaceutically acceptable carrier.

A "pharmaceutically effective amount" is described in detail below.

In a further aspect the invention relates to a method of producing a vaccine for fish, by admixing the polypeptide, protein, carrier, or nucleic acid according to the invention with a pharmaceutically acceptable carrier.

A "pharmaceutically acceptable carrier" can e.g. be water, saline, or a buffer suitable for the purpose. In a more complex form the formulation may comprise an emulsion which itself comprises other compounds, such as a cytokine, an adjuvant, an additional antigen, etc.

The vaccine according to the invention can be used both for prophylactic and for therapeutic treatment.

In a preferred embodiment the vaccine according to the invention additionally comprises an adjuvant.

An adjuvant is an immunostimulatory substance boosting the immune response of the host in a non-specific manner. Many different adjuvants are known in the art. Examples of adjuvants frequently used in fish farming are muramyldipeptides, lipopolysaccharides, several glucans and glycans and CARBOPOL® (a homopolymer). An extensive overview of adjuvants suitable for fish vaccines is given in the review paper by Jan Raa (1996, Reviews in Fisheries Science, vol. 4, p. 229-288).

Suitable adjuvants are e.g. water in oil (w/o) emulsions, o/w emulsions and w/o/w double-emulsions. Oil adjuvants suitable for use in w/o emulsions are e.g. mineral oils or metabolisable oils. Mineral oils are e.g. BAYOL®, MARCOL® and DRACOL®; metabolisable oils are e.g. vegetable oils, such as peanut oil and soybean oil, or animal oils such as the fish oils squalane and squalene. Alternatively a vitamin E (tocopherol) solubilisate as described in EP 382,271 may advantageously be used.

Very suitable o/w emulsions are e.g. obtained starting from 5-50% w/w water phase and 95-50% w/w oil adjuvant, more preferably 20-50% w/w water phase and 80-50% w/w oil adjuvant are used.

The amount of adjuvant added depends on the nature of the adjuvant itself, and information with respect to such amounts provided by the manufacturer.

In a preferred embodiment the vaccine according to the invention additionally comprises a stabiliser.

A stabilizer can be added to a vaccine according to the invention e.g. to protect it from degradation, to enhance the shelf-life, or to improve freeze-drying efficiency. Useful stabilizers are i.a. SPGA (Bovarnik et al, 1950, J. Bacteriology, vol. 59, p. 509), skimmed milk, gelatine, bovine serum albumin, carbohydrates e.g. sorbitol, mannitol, trehalose, starch, sucrose, dextran or glucose, proteins such as albumin or casein or degradation products thereof, and buffers, such as alkali metal phosphates.

In addition, the vaccine may comprise one or more suitable surface-active compounds or emulsifiers, e.g., SPAN® or TWEEN®.

The vaccine may also comprise a so-called "vehicle". A vehicle is a compound to which the polypeptide or the protein according to the invention adheres, without being covalently bound to it. Such vehicles are i.a. bio-microcapsules, microalginates, liposomes and macrosols, all known in the art. A special form of such a vehicle is an Iscom, described above.

It goes without saying that admixing other stabilizers, carriers, diluents, emulsions, and the like to vaccines according to the invention are also within the scope of the invention. Such additives are for instance described in well-known handbooks such as: "Remington: the science and practice of pharmacy" (2000, Lippincot, USA, ISBN: 683306472), and:

"Veterinary vaccinology" (P. Pastoret et al ed., 1997, Elsevier, Amsterdam, ISBN: 0444819681).

For reasons of e.g. stability or economy a composition according to the invention may be freeze-dried. In general this will enable prolonged storage at temperatures above zero ° C., e.g. at 4° C. Procedures for freeze-drying are known to persons skilled in the art, and equipment for freeze-drying at different scales is available commercially.

Therefore, in a preferred embodiment, the vaccine according to the invention is in a freeze-dried form.

To reconstitute a freeze-dried composition, it is suspended in a physiologically acceptable diluent. Such a diluent can e.g. be as simple as sterile water, or a physiological salt solution. In a more complex form the freeze-dried vaccine may be suspended in an emulsion e.g. as described in EP 1,140,152.

A vaccine according to the invention may take any form that is suitable for administration in the context of aqua-culture farming, and that matches the desired route of application and desired effect. Preparation of a vaccine according to the invention is carried out by means conventional for the skilled person.

Preferably the vaccine according to the invention is formulated in a form suitable for injection or for immersion vaccination, such as a suspension, solution, dispersion, emulsion, and the like. Commonly such vaccines are prepared sterile.

Target animal for the vaccine according to the invention is a fish, preferably a salmonid fish, more preferably a rainbow trout (*Oncorhynchus mykiss*) or an Atlantic salmon (*Salmo salar* L.)

The dosing scheme of the application of a vaccine according to the invention to the target organism can be in single or multiple doses, which may be given at the same time or sequentially, in a manner compatible with the dosage and formulation, and in such an amount as will be immunologically effective.

It is well within the capacity of the skilled person to determine whether a treatment is "immunologically effective", for instance by administering an experimental challenge infection to vaccinated animals, and next determining a target animals' clinical signs of disease, serological parameters, or by measuring reisolation of the pathogen.

What constitutes a "pharmaceutically effective amount" for a vaccine according to the invention that is based upon a polypeptide, a protein, a carrier, or a nucleic acid according to the invention, is dependent on the desired effect and on the target organism. Determination of the effective amount is well within the skills of the routine practitioner.

A preferred amount of a polypeptide or a protein according to the invention, comprised in a pharmaceutical composition according to the invention, is between 1 ng and 1 mg per animal dose. More preferably the amount is between 10 ng and 100 µg/dose, even more preferably between 100 ng and 10 µg/dose. A dose exceeding 1 mg, although immunologically very suitable, will be less attractive for commercial reasons.

A preferred amount of a nucleic acid, a DNA fragment, or a recombinant DNA molecule according to the invention, comprised in a pharmaceutical composition according to the invention, has been described above.

A preferred amount of a live recombinant carrier according to the invention, comprised in a vaccine according to the invention, is dependent on the characteristics of the carrier micro organism used. Such an amount is expressed for instance as plaque forming units (pfu), colony forming units (cfu) or tissue culture infective dose 50% ($TCID_{50}$), depending on what is a convenient way of quantifying the LRC organism. For instance for a live viral vector a dose range between 1 and $10^{10}$ plaque forming units (pfu) per animal dose may advantageously be used; preferably a range between $10^2$ and $10^6$ pfu/dose.

A preferred amount of a host cell according to the invention, comprised in a vaccine according to the invention, is between 1 and $10^9$ host cells per animal dose. More preferably between 10 and $10^7$ cells/dose are used.

Many ways of administration can be applied, all known in the art. The vaccines according to the invention are preferably administered to the fish via injection, immersion, dipping or per oral. The protocol for the administration can be optimized in accordance with standard vaccination practice. An overview of fish vaccination by Bowden et al. (Fisheries Research Service Marine Laboratory, Aberdeen, Scotland) is available as an Industry Report of 27 Mar. 2003.

Preferably the vaccine is administered via immersion or per oral. This is especially efficient in case of the use of such vaccines in the setting of commercial aqua-culture farming.

Preferred embodiments on the use of carriers in oral vaccination have been described above.

The age, and therefore the weight, of the fish to be vaccinated is not critical, although it is evidently favourable to vaccinate against SAV as early as possible to prevent a field infection. Juvenile salmonids can be vaccinated already at 0.2 grams, and but before reaching 5 grams of weight. Fish having a weight of less than 0.5 grams however are assumed to be insufficiently immune competent. Therefore, in practice, one would try to vaccinate fish having a weight of between 0.5 and 5 grams. Since it is one of the merits of the present invention that it is now possible to perform early diagnosis of SAV, control measurements such as sanitation can be developed in order to postpone or reduce outbreaks in the geographical area, until fish have been vaccinated.

It is highly efficient to formulate a vaccine according to the invention as a combination-vaccine, that is by combining a polypeptide, protein, carrier, or nucleic acid according to the invention, with at least one other fish-pathogenic micro organism or virus, with an antigen of such micro organism or virus, or with a nucleic acid encoding such an antigen.

Therefore, in a preferred embodiment, the vaccine according to the invention is a combination vaccine.

The advantage of such a combination vaccine is that it not only provides protection against SAV, but also against other diseases, while only one vaccination manipulation is required, thereby preventing needless stress to the animals as well as time- and labour costs.

In a more preferred embodiment the combination vaccine according to the invention comprises at least one other micro organism or virus that is pathogenic to fish, preferably to salmonids, or one other antigen from a virus or micro organism pathogenic to fish, or a nucleic acid encoding said other antigen.

Therefore, in an even more preferred embodiment of the combination vaccine according to the invention, the other micro organism or virus, or the antigen, or the nucleic acid encoding said other antigen, is selected from the group consisting of *Aeromonas salmonicida* subsp. *salmonicida*, *Vibrio anguillarum*, *V. anguillarum* serovar O1 and serovar O2, *V. salmonicida*, *Moritella viscosa* (=*V. viscosus*), *Photobacterium damselae* subspecies *piscicidae*, *Tenacibaculum maritimum*, *Yersinia ruckeri*, *Piscirickettsia salmonis*, *Renibacterium salmoninarum*, *Lactococcus garvieae*, *Flavobacterium* sp., *Flexibacter* sp., *Streptococcus* sp., *Lactococcus garviae*, *Edwardsiella tarda*, *E. ictaluri*, Infectious Pancreatic Necrosis Virus, Infectious Salmon Anaemia virus, Nervous Necrosis Virus, and Heart and skeletal muscle inflammation.

The disease Heart and skeletal muscle inflammation (HSMI) is a recently described salmonid disease of viral origin (Kongtorp et al, 2004, J. of Fish diseases, vol. 27, p. 351-358).

The vaccines according to the invention, described above, contribute to active vaccination, i.e. they trigger the host's defence system. Alternatively, virus neutralising antibodies can be raised against the polypeptide, the protein, or the carrier according to the invention, as outlined above. Such VN antibodies can then be administered to the fish. This method of vaccination, so-called passive vaccination, is the vaccination of choice when an animal is already infected, and there is no time to allow the natural immune response to be triggered. It is also the preferred method for vaccinating animals that are prone to sudden high infection pressure. The administered VN antibodies neutralise SAV, which has the great advantage that it decreases or stops the establishment or progression of an SAV infection almost immediately, independent of the fish's immune status.

Therefore, in an alternate aspect, the invention provides a vaccine comprising salmonid alphavirus neutralising antibodies.

A vaccine can also be prepared using antibodies prepared from eggs of chickens that have been vaccinated with a vaccine according to the invention (IgY antibodies).

Preferably a vaccine for oral administration of the antibodies is prepared, in which the antibodies are mixed with an edible carrier such as fish feed.

In another aspect, the invention relates to a diagnostic test kit comprising a polypeptide, a protein, a carrier, or a nucleic acid according to the invention.

As mentioned above, mortality after SAV infection can be up to 60%. Thus, for efficient protection and control measures against SAV and its induced disease, a quick and specific diagnosis of SAV is important.

Therefore it is another objective of this invention to provide diagnostic tools suitable for the detection of SAV.

A diagnostic test kit for the detection of antigenic material comprising an SAV E2 VN epitope according to the invention is suitable and specific for the detection of all SAV subtypes.

Such a test may e.g. comprise a standard antigen ELISA test, wherein the wells of an ELISA plate are coated with an antibody directed against the SAV E2 VN epitope. Such antibodies are reactive with the SAV E2 VN epitope as comprised in the polypeptide, the protein, or the carrier according to the invention, and can be obtained as described above. After incubation with the material to be tested, labelled antibodies reactive with the SAV E2 VN epitope are added to the wells. A colour reaction then reveals the presence of bound antigenic material of SAV. Protocols for labelling antibodies by coupling of a fluorescent group to the immunoglobulin or another marker, are well known in the art.

Also, a diagnostic test kit for the detection in a sample or in an animal serum of antibodies reactive with the SAV E2 VN epitope according to the invention is suitable and specific for the detection of an immune response against SAV of any of the subtypes.

Such a test may e.g. comprise a standard antibody ELISA test. In such a test the wells of an ELISA plate can e.g. be coated with the SAV E2 VN epitope comprised in a polypeptide, a protein, or a carrier according to the invention. After incubation with the material to be tested, labelled antibodies reactive with the immunoglobulins of the test sample (if present) are added to the wells. A colour reaction then reveals the presence in the test sample of antibodies reactive with the SAV E2 VN epitope according to the invention.

Therefore, in an embodiment the invention relates to diagnostic test kits for the detection of antibodies reactive with the SAV E2 VN epitope. Such test kits comprise the polypeptide, the protein, or the carrier according to the invention.

The design of such an immunoassay may vary. For example, the immunoassay may also be based upon competition, in stead of on direct binding. Furthermore, such tests may also use particulate or cellular material, in stead of the solid support of a device. The detection of the antibody-antigen complex formed in the test may involve the use of labelled antibodies, wherein the labels may be, for example, enzymes or fluorescent-, chemo luminescent-, radio-active- or dye molecules.

Suitable methods for the detection of antibodies reactive with the SAV E2 VN epitope according to the invention in a sample include the enzyme-linked immunosorbent assay (ELISA), immunofluorescence test (IFT) and Western blot analysis.

A quick and easy diagnostic test for diagnosing the presence or absence of SAV is a PCR test as described above, comprising primers specifically hybridising to a nucleic acid in a test sample that is similar to a nucleic acid according to the invention. Such primers are for instance the following two, giving a product of 188 nucleotides, from within the SAV E2 VN epitope of the invention:

```
FWD: 5'-TTGACGTGTACGACGCTCTG-3'        (SEQ ID NO: 9)
REV: 5'-AACCGGCTCCTCACACGTAAAC-3'      (SEQ ID NO: 10)
```

The nucleic acid, DNA fragment, recDNA molecule, or carrier according to the invention can advantageously be used in such PCR test as a positive standard.

Alternatively, such a diagnostic test may use the nucleic acid, DNA fragment, recDNA molecule, or carrier according to the invention, in a set up using hybridisation without amplification to e.g. a membrane or a device.

The invention will now be further described with reference to the following, non-limiting, examples.

EXAMPLES

Example 1

Cloning

An SPDV E3E2 sequence was obtained from an SAV subtype 3 isolate: an SPDV infected Atlantic salmon was sampled from an aquaculture farm in Norway (Mølsvik). From its heart tissue a total RNA extract was prepared using an ABSOLUTELY RNA MINIPREP KIT(Stratagene), according to the manufacturer's instructions. From the cDNA prepared, the total E3E2 coding region was amplified with RT-PCR primers. The primers used were:

For the reverse transcription, the following primer was used:

```
                                       (SEQ ID NO: 11)
RTE2: 5'-CCGCGCGAGCCCCTGGTATGCAACACAGTGC-3'
```

Next, high fidelity PCR amplification was performed, using pfu turbo polymerase (Stratagene), with the primer set:

```
RT-E2 XhoI:
                                       (SEQ ID NO: 12)
5'-ATACCAGGGGCTCGCGCCTCGAGACCCTACTTG-3'

PCR-E3 HindIII:
                                       (SEQ ID NO: 13)
5'-GATGCCATAAGCTTGACACGCGCTCCGGCCCTC-3'
```

Finally the sequence of the E3E2 gene was determined by sequencing with these two PCR primers, and two internal primers:

```
                                       (SEQ ID NO: 14)
PD5: 5'-CGTCACTTTCACCAGCGACTCCCAGACG-3'

(SEQ ID NO: 15)
PD3: 5'-GGATCCATTCGGATGTGGCGTTGCTATGG -3'
```

Sequencing was performed with BIG DYE 3.1® (Applied Biosystems), according to the manufacturer's instructions.

The complete nucleotide sequence for the E2 encoding region of the Mølsvik SAV isolate will be published under accession number DQ 195447, but for the invention all relevant sequences have been indicated herein.

Once verified by sequencing, the E3E2 PCR product was digested overnight with the restriction enzymes XhoI and HindIII, and cloned in the corresponding unique sites of the pET30a(+) vector (Novagen) leading to the construct pET30a/E3E2.

Subcloning of Regions Derived from SAV E2:

From the Mølsvik SAV E2 sequence, various shorter sequences were obtained using a subcloning strategy, in which PCR of a set of primers hybridising at various positions on the E2 gene was employed. The PCR primers used to amplify fragments of the SAV E2 encoding region (using the construct pET30a/E3E2 as template) are listed in Table 3, and were designed as follows:
- forward primers start with 3-5 random A or T nucleotides, followed by an NdeI restriction site. Next come 16 to 20 matching nucleotides, the length is optimised depending on the specific local sequence, and selected to start the PCR fragment at a desired nucleotide. Primers are 24 to 30 nucleotides in total.
- reverse primers also comprise 3-5 random at nucleotides, but are followed by an NcoI restriction site, and then 16-20 specific nucleotides.

TABLE 3

Primers used herein, for making fragments of SAV E2.

| Forward primer | expressed E2 fragment starts at aa | SEQ ID NO: |
|---|---|---|
| Frag5-fwd | 111 | 16 |
| F1 | 139 | 17 |
| F2 | 158 | 18 |
| F3 | 177 | 19 |

TABLE 3-continued

Primers used herein, for making fragments of SAV E2.

| Reverse primer | expressed E2 fragment ends at aa | SEQ ID NO: |
|---|---|---|
| Frag5-rev | 304 | 20 |
| R1 | 290 | 21 |
| R2 | 270 | 22 |
| R3* | 252 | 23 |
| R4 | 231 | 24 |

Fragments produced in PCR were digested overnight with NdeI and NcoI, and cloned into the pET30a(+) bacterial expression plasmids (Novagen).

Because the NdeI restriction site incorporates an ATG start codon, expression started on this Methionine.

Cloned sequences were verified by DNA sequencing using the standard pET-T7 promoter primer: 5'-AATACGACT-CACTATAGGG-3' (SEQ ID NO: 25) and standard T7 terminator primer: 5'-GCTAGTTATTGCTCAGCGG-3' (SEQ ID NO: 26) in order to obtain overlapping contigs covering the whole cloned sequence.

Subcloned fragments of SAV E2 were expressed in E. coli, and the protein fragments produced were used in in vivo and in vitro experiments to test the SAV E2 VN epitope of the invention.

Recombinant proteins were also expressed as fusion proteins using the pET30a(+) plasmids, by cloning these in frame with a 6×His tag or a β-gal gene (LacZ), inserted into a pET30a(+) plasmid.

In order to construct the pET30a/LacZ vector, the lacZ gene contained in the vector pVAX1/LacZ (Invitrogen) was amplified by PCR using the primers:

```
LacZ'_NcoI:
                                       SEQ ID NO: 27
5'-GTATGCCCATGGAACGTCGTTTTACAACGTCGTG-3'

LacZ'_XhoI:
                                       SEQ ID NO: 28
5'-GTCTCGCTCGAGTTATTTTTGACACCAGACCAACTGG-3'
```

Following overnight digestion with NcoI and XhoI, the digested PCR product was cloned into the corresponding restriction sites of the pET30a(+) plasmid. Digestion of this pET30a/LacZ construct with NdeI/NcoI allowed the in frame insertion of the described E2 subfragments digested with NdeI/NcoI.

Example 2

Expression

Expression of the various E2 fragments was done in BL21 Rosetta 2 E. coli cells. The pET3a plasmids containing the various E2 gene fragments were used to transform Rosetta 2 cells (Novagen), according to the suppliers instructions. An overnight pre-culture (20 ml) of transformed E. coli was used next day to inoculate 800 ml cultures with 5 ml pre-culture. When the OD600 was at approximately 0.7, then IPTG was added to 1 mM final concentration for induction of expression. This was cultured for another 2 hours. Then cultures were centrifuged at 7000 rpm for 5 min, and bacterial cell pellet was kept at −80° C. until use.

Purification:

To purify the inclusion bodies, two buffers were used:
buffer A = 50 mM tris/HCl pH8.00 +2 mM EDTA
buffer B = buffer A +1% (final concentration) Triton X-100 TRITON X -100®

Then, for the cell pellet of an 800 ml culture: the cell pellet was resuspended in 50 ml of buffer A and add freshly prepared lysozyme (from a stock at 10 mg/ml) to a final concentration of 100 µg/ml. 25 ml of buffer B was then added and 10 µl of BENZONASE® (MERCK). This was incubated at 30° C. for 15 min with gentle shaking for removal of DNA.

Next 100 ml buffer B was added and the mixture was sonicated for 4×30 seconds. The sonicate was centrifuged at 12.000×g for 20 min. at 4° C. The inclusion body pellet was washed with 250 ml of buffer B, and with 200 ml of PBS. Finally the pellet containing the rec E2 protein fragments were resuspended in 40 ml (4×10 ml) of PBS, and kept at −80° C. until use.

Recombinant *E. coli* proteins were quantified by scanning and analysis of samples run on SDS-PAA gels that had been stained with Coomassie bb., in relation to lanes with marker protein, according to standard procedures.

Example 3

Testing and Use

Monoclonal Antibody:

For testing the recombinant SAV E2 protein fragments, an SAV neutralising monoclonal antibody was used. This had been produced by immunising Balb/c mice with $10^{10}$ SAV virus strain S49P in Freund's complete adjuvant, obtained from an polyethylene glycol concentrated CHSE-214 cell culture supernatant. Booster injections were given, with Freund's incomplete adjuvant, and without adjuvant, using standard techniques. Mice spleen cells were fused with $Sp_2O$ tumour cells, and resulting hybridomas were selected in HAT medium. Monoclonal antibodies (Mab's) produced were selected for binding to SAV virus on SAV infected CHSE-214 cells by immunofluorescence using standard techniques. Positives were tested in a virus neutralisation assay. The hybridoma cells producing VN positive Mab's were scaled up by making ascites in mice using standard procedures.

Immunofluorescence assay (WA):

IFA was performed on SAV infected CHSE-214 cells, and on pET plasmid transfected *E. coli* cells expressing the rec protein of interest, with proper positive and negative controls. Cells were fixed in ethanol 96%:acetone 1:1 at −20° C. for 30 minutes, and rinsed 3 times with PBST (PBS 1+0,05% TWEEN 20. The primary antibody, diluted in PBST was added and incubated 1 hour at room temperature. Next plates were rinsed with PBST, and the second antibody was applied: an FITC conjugated anti-mouse antibody. After incubation and wash, each well was scored through observation with an immunofluorescence microscope with the appropriate UV light filter. The infected cells reacting positively with the primary antibody appeared fluorescent.

Figure 5:
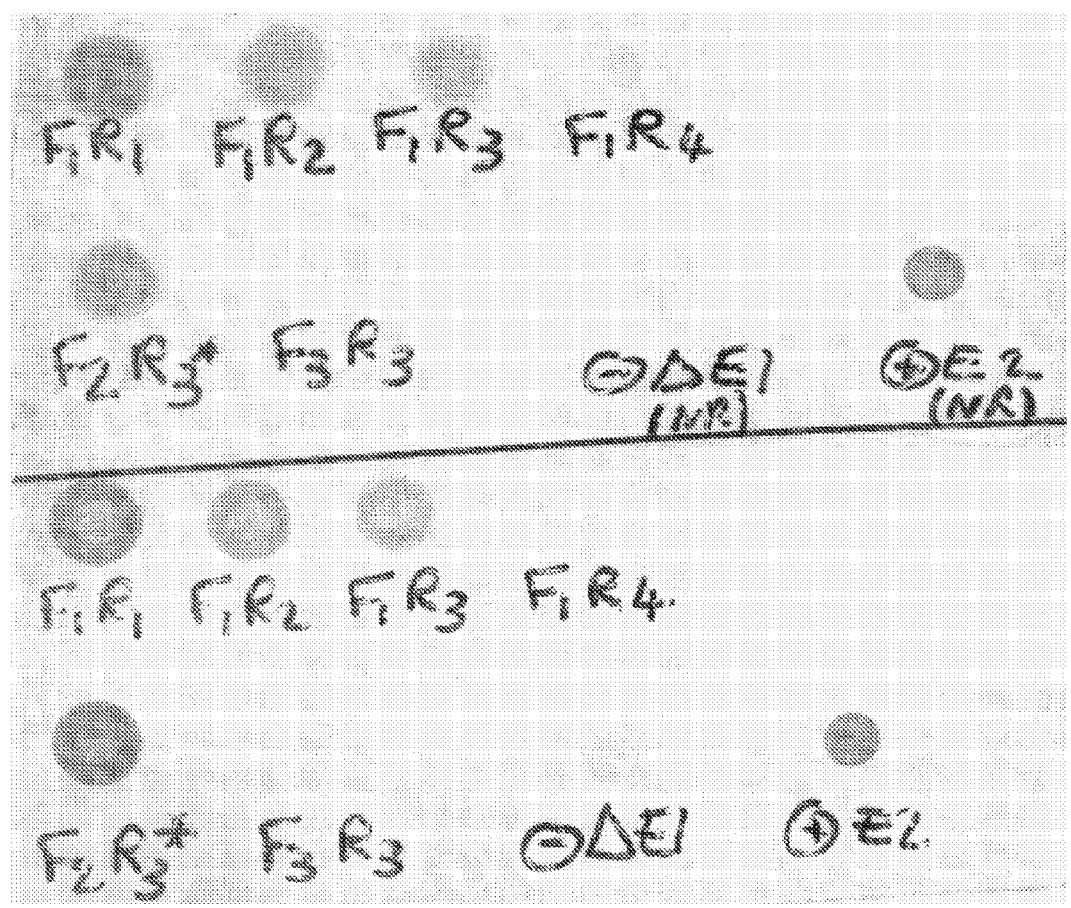

Immuno-blotting:

For Western blotting samples were run on 10% SDS/PAA gels (NUPAGE®, NOVEX), and blotted onto nitrocellulose according to the manufacturers instructions. For dot blot, 5 µl samples were spotted on membranes directly with a pipette, and left to dry for 5-10 minutes. Next, the membrane was blocked with Tris buffered saline +0.05% Tween 20 (TBST) +5% skimmed milk, O/N at 4° C. The membrane is incubated with the primary antibody, diluted to the appropriate concentration in TBST+1% skimmed milk, for 1 hr at room temperature. Then after 3 washes in TBST, the membrane is incubated with the secondary antibody, an alkaline phosphatase conjugated Goat anti-mouse IgG in TBST. After washing with TBST, alkaline phosphatase colouring reaction was performed with Alkaline Phosphatase Conjugate Substrate Kit according to the manufacturer's instructions (BioRad). Reaction was stopped with distilled water, membranes were dried and digitized. ps Results of immunoblotting with the polypeptides and proteins according to the invention is presented in FIGS. 5 an 6:

FIG. 5 shows a dot blot of various polypeptides and proteins according to the invention, stained with an SAV neutralising monoclonal.

Positive recognition was found for
the positive control, full length SAV E2 protein,
polypeptides F1R1, F1R2, F1R3, and F2R3*

Negative response was detected for:
the negative control SAV E1 protein
the polypeptides F1R4 and F3R3

This ratio of positive and negatives was observed both when the samples had been denatured in a sample buffer containing β-mercaptoethanol and dithiothreitol, and were boiled before spotting (upper panel), as when the samples were taken up in a non-denaturing sample buffer, and were not boiled (lower panel).

Figure 6:
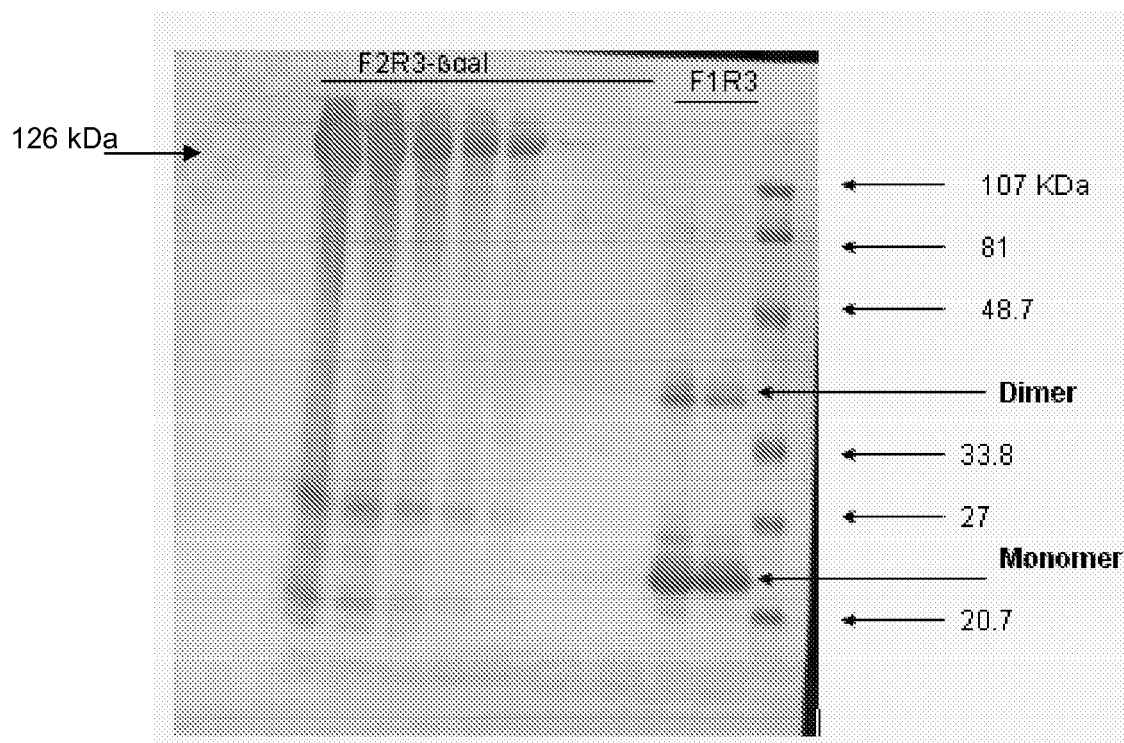

FIG. 6 shows a Western blot of a polypeptide according to the invention made with primers F1 and R3, thus covering the part of SAV E2 from aa 139-290; and of a protein according to the invention, the SAV E2 fragment made with primers F2 and R3, thus spanning aa 158-252, in a fusion construct with β-gal protein. The blot was incubated with an SAV neutralising Mab, and several specific bands were detected.

Bands detected in the F1R3 lanes are at 22 and 44 kDa, probably a monomer and a dimer form of the polypeptide.

NB: although the calculated weight of the polypeptide is only 15 kDa, on the gel this band runs slower, most likely because of the presence of disulfide bridges that were not completely denatured in the sample preparation.

The F2R3-βgal lanes show a band of approximately 126 kDa, representing the fusion protein of F2R3 (10 kDa) and β-gal (116 kDa).

VN Assay:

Equal volumes of a dilution of the SAV neutralising Mab and of 100 $TCID_{50}$ of an SAV sample in EMEM culture medium with 2% serum, were mixed in a micro titration plate and incubated 2 hours at 20° C. SAV isolates from all subtypes were used in VN assay (F93-125 [subtype 1], S49P [2], and PD03-08 [3]). Next CHSE-214 cells in EMEM culture medium with 5% serum were added to a density of 2.5×10⁻s/ml. The plates were incubated in $CO_2$ incubators for 5-7 days at 15° C.

After 5-7 days the plates were read by light microscopy, identifying cells with cytopathic effect (cpe), indicating the dilution of the Mab not able to completely neutralise the test virus. Cpe was positive when clumps of cells were observed that had rounded off, and became more refringent.

Alternatively cells were fixed in ethanol/acetone, rinsed with PBST, and stained in IFA as described, while using as primary antiserum, a polyclonal rabbit antiserum raised against SPDV E1 protein (serum AB06).

In a typical experiment, the results of a VN test on F93-195, and PD03-08, read by cpe showed full viral neutralisation by the SAV neutralising Mab ascites up to a dilution of 32.000. This was confirmed by IFA.

Animal trial:

In an animal trial juvenile Atlantic salmon were vaccinated with proteins according to the invention. Proteins used were F2R3 fused to β-gal, and F1R3 fused to a 6× Histidine tag. In short: proteins were expressed in E. coli and purified as described. Protein was formulated to 30% water-in-oil emulsion with Montanide ISA 763A. Animals were vaccinated with 150 μg/dose and boosted with 100 μg/dose. Positive control was the commercial inactivated SPDV vaccine NORVAX® COMPACT PD . Negative controls were: saline, emulsion without protein, and β-gal without fusion.

Test animals were Atlantic salmon smolts of circa 40 grams, that were acclimatised in the test facility for 1 week, and were then vaccinated intra-peritoneal using standard procedure. Regular blood sampling was applied. After 5 weeks the fish received the booster vaccination and after an additional 3 weeks the fish will be challenged using a dose of $10^3$ $TCID_{50}$/animal of PD03-08 (SAV subtype 3). Protective capacity will be scored by analysing clinical signs of disease, serology, gross pathology and histology.

Antibody Elisa:

An Elisa test was set up, to detect anti-SAV antibodies in salmon serum. General procedure was as described above; briefly: an SAV neutralising Mab was coated to micro titration wells, incubated with a standard SPDV sample and washed. Salmon serum was applied in PBST+1% skimmed milk, in a serial dilution in duplo. Appropriate positive and negative controls were applied. Incubation was overnight at 4° C. next the plates were washed and incubated with a rabbit polyclonal anti-salmon serum. Finally a third antibody is incubated: goat anti-rabbit, conjugated to HRP. Finally calorimetric detection was done by using an HRPsubstrate and $H_2O_2$, according to the manufacturer's instructions.

Typically, SAV antibodies could be detected with good specificity and sensitivity in sera from SPDV infected salmon.

LEGEND TO THE FIGURES

FIG. 1:
Graphical representation of the length and position of the various protein sequences described herein, relative to the corresponding regions of the full length SAV E2 protein.

FIGS. 2, 3, 4:
Multiple alignment of the regions of aa 158-252, 139-290, or 111-304 respectively, of several SAV E2 proteins. Entries are identified by accession number, and are described in Table 1. Reference strain is SPDV isolate N3 (acc. nr: AAU01400.1). The consensus sequence from the multiple alignment of these regions equals SEQ ID NO: 4, 5, or 6.
Numbers above the sequences indicate the number of the amino acids corresponding to SAV E2; numbers below the consensus sequences indicate the total length of the polypeptides.

FIG. 5:
Dot blot of several polypeptides and proteins, stained with an SAV neutralising monoclonal antibody. Upper panel: denatured samples, lower panel: non-denatured.

FIG. 6:
Western blot of polypeptide F1R3, and of protein F2R3-βgal, stained with an SAV neutralising monoclonal antibody.

The invention claimed is:

1. A salmonoid alphavirus (SAV) polypeptide comprising an amino acid sequence having at least 90% amino acid identity to SEQ ID NO: 3 wherein the polypeptide is at least 95 and at most 166 amino acids in size.

2. A recombinant protein comprising a polypeptide according to claim 1, wherein, except for the polypeptide of claim 1, said protein is not a salmonid *alphavirus* (SAV) E2 protein and said recombinant protein being more than 166 amino acids in size.

3. A SAV polypeptide that is a part of a SAV E2 protein, wherein the polypeptide comprises at least the 95 amino acid sequence of SEQ ID NO: 4 and at most the 194 amino acid sequence of SEQ ID NO: 6.

4. A recombinant protein comprising a polypeptide according to claim 3, wherein, except for the polvpeptide of claim 3, said protein is not a SAV E2 protein and said recombinant protein being larger in size than said polypeptide.

5. A carrier comprising a protein according to claim 2.

6. A method of producing salmonid *alphavirus* neutralising antibodies, comprising the steps of a) administering a polypeptide according to claim 1 to an animal,
b) obtaining serum from the animal, and
c) isolating antibodies reactive with the polypeptide from the serum.

7. Nucleic acid encoding a polypeptide according to claim 1.

8. Carrier comprising a nucleic acid according to claim 7, whereby said carrier is selected from the group consisting of a DNA fragment, a recombinant DNA molecule, a live recombinant carrier, and a host cell.

9. Vaccine comprising a polypeptide according to claim 1 and a pharmaceutically acceptable carrier.

10. Diagnostic kit comprising a polypeptide according to claim 1.

11. The polypeptide of claim 1, having the amino acid sequence of SEQ ID NO: 1.

12. The polypeptide of claim 1, having the amino acid sequence of SEQ ID NO: 2.

* * * * *

SEQUENCE LISTING

<160> NUMBER OF SEQ ID NOS: 28

<210> SEQ ID NO 1
<211> LENGTH: 95
<212> TYPE: PRT
<213> ORGANISM: Salmonid alphavirus subtype 1

<400> SEQUENCE: 1

Asp Met Thr Lys Lys Cys Thr Arg Phe Ser Thr Thr Pro Lys Lys Ser
1               5                   10                  15

Ala Leu Tyr Leu Val Asp Val Tyr Asp Ala Leu Pro Ile Ser Val Glu
            20                  25                  30

Ile Ser Thr Val Val Thr Cys Ser Asp Ser Gln Cys Thr Val Arg Val
        35                  40                  45

Pro Pro Gly Thr Thr Val Lys Phe Asp Lys Lys Cys Lys Ser Ala Asp
    50                  55                  60

Ser Ala Thr Val Thr Phe Thr Ser Asp Ser Gln Thr Phe Thr Cys Glu
65                  70                  75                  80

Glu Pro Val Leu Thr Ala Ala Ser Ile Thr Gln Gly Lys Pro His
                85                  90                  95

<210> SEQ ID NO 2

```
<211> LENGTH: 95
<212> TYPE: PRT
<213> ORGANISM: Salmonid alphavirus subtype 2

<400> SEQUENCE: 2

Asp Leu Thr Lys Lys Cys Thr Arg Phe Ser Thr Thr Pro Lys Lys Ser
1               5                   10                  15

Ala Leu Tyr Leu Val Asp Val Tyr Asp Ala Leu Pro Thr Ser Val Glu
            20                  25                  30

Ile Ser Thr Val Val Thr Cys Asn Glu Arg Gln Cys Thr Val Arg Val
        35                  40                  45

Pro Pro Gly Thr Thr Val Lys Phe Asp Lys Arg Cys Lys Asn Ala Ala
    50                  55                  60

Lys Glu Thr Val Thr Phe Thr Ser Asp Ser Gln Thr Phe Thr Cys Glu
65                  70                  75                  80

Glu Pro Val Leu Thr Ala Ala Ser Ile Thr Gln Gly Lys Pro His
                85                  90                  95

<210> SEQ ID NO 3
<211> LENGTH: 95
<212> TYPE: PRT
<213> ORGANISM: Salmonid alphavirus subtype 3

<400> SEQUENCE: 3

Asp Leu Thr Lys Lys Cys Thr Arg Phe Ser Thr Thr Pro Lys Lys Ser
1               5                   10                  15

Ala Pro Tyr Leu Val Asp Val Tyr Asp Ala Leu Pro Ile Ser Val Glu
            20                  25                  30

Ile Ser Thr Val Val Thr Cys Asn Asp Asn Gln Cys Thr Val Arg Val
        35                  40                  45

Ser Pro Gly Thr Thr Val Lys Phe Asp Lys Lys Cys Lys Ser Ala Ala
    50                  55                  60

Gln Ala Thr Val Thr Phe Thr Ser Asp Ser Gln Thr Phe Thr Cys Glu
65                  70                  75                  80

Glu Pro Val Leu Thr Ala Ala Ser Ile Thr Gln Gly Lys Pro His
                85                  90                  95

<210> SEQ ID NO 4
<211> LENGTH: 95
<212> TYPE: PRT
<213> ORGANISM: Salmonid alphavirus
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (40)..(42)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
```

```
<220> FEATURE:
<221> NAME/KEY: misc_feature
<222> LOCATION: (59)..(59)
<223> OTHER INFORMATION: Xaa can be any naturally occurring amino acid
<220> FEAT

```
<221> NAME/KEY: misc_feature
<222> LOCATION: (146)..(146)
<223> OTHER INFORMATION: Xaa can be any naturally occurring amino acid

<400> SEQUENCE: 5

Glu His Gln Val Thr Glu Lys Phe Thr Arg Glu Arg Ser Lys Gly His
1               5                   10                  15

His Leu Ser Asp Xaa Thr Lys Lys Cys Thr Arg Phe Ser Thr Thr Pro
            20                  25                  30

Lys Lys Ser Ala Xaa Tyr Leu Val Asp Val Tyr Asp Ala Leu Pro Xaa
        35                  40                  45

Ser Val Glu Ile Ser Thr Val Val Thr Cys Xaa Xaa Xaa Gln Cys Thr
50                  55                  60

Val Xaa Val Xaa Pro Gly Thr Thr Val Lys Phe Asp Lys Xaa Cys Lys
65                  70                  75                  80

Xaa Ala Xaa Xaa Xaa Thr Val Thr Phe Thr Ser Asp Ser Gln Thr Phe
                85                  90                  95

Thr Cys Glu Glu Pro Val Leu Thr Ala Ala Ser Ile Thr Gln Gly Lys
            100                 105                 110

Pro His Leu Arg Ser Xaa Met Leu Pro Ser Gly Gly Lys Glu Val Lys
        115                 120                 125

Ala Arg Ile Pro Phe Pro Phe Pro Glu Thr Ala Thr Cys Arg Val
130                 135                 140

Ser Xaa Ala Pro Leu Pro Ser Ile
145                 150

<210> SEQ ID NO 6
<211> LENGTH: 194
<212> TYPE: PRT
<213> ORGANISM: Salmonid alphavirus
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (87)..(89)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
```

```
<222> LOCATION: (109)..(109)
<223> OTHER INFORMATION: Xaa can be any naturally occurring amino acid
<220> FEATURE:
<221> NAME/KEY: misc_feature
<222> LOCATION: (111)..(113)
<223> OTHER INFORMATION: Xaa can be any naturally occurring amino acid
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
<222> LOCATION: (174)..(174)
<223> OTHER INFORMATION: Xaa can be any naturally occurring amino acid

<400> SEQUENCE: 6

Ile Leu Ala Xaa Cys Pro Xaa Gly Gln Ser Xaa Thr Val Ala Ala Thr
 1               5                  10                  15

Leu Asp Gly Thr Arg His Gln Cys Thr Thr Val Phe Glu His Gln Val
            20                  25                  30

Thr Glu Lys Phe Thr Arg Glu Arg Ser Lys Gly His His Leu Ser Asp
        35                  40                  45

Xaa Thr Lys Lys Cys Thr Arg Phe Ser Thr Thr Pro Lys Lys Ser Ala
 50                  55                  60

Xaa Tyr Leu Val Asp Val Tyr Asp Ala Leu Pro Xaa Ser Val Glu Ile
65                   70                  75                  80

Ser Thr Val Val Thr Cys Xaa Xaa Xaa Gln Cys Thr Val Arg Val Xaa
                85                  90                  95

Pro Gly Thr Thr Val Lys Phe Asp Lys Xaa Cys Lys Xaa Ala Xaa Xaa
            100                 105                 110

Xaa Thr Val Thr Phe Thr Ser Asp Ser Gln Thr Phe Thr Cys Glu Glu
            115                 120                 125

Pro Val Leu Thr Ala Ala Ser Ile Thr Gln Gly Lys Pro His Leu Arg
        130                 135                 140

Ser Xaa Met Leu Pro Ser Gly Gly Lys Glu Val Lys Ala Arg Ile Pro
145                 150                 155                 160

Phe Pro Phe Pro Pro Glu Thr Ala Thr Cys Arg Val Ser Xaa Ala Pro
                165                 170                 175

Leu Pro Ser Ile Thr Tyr Glu Glu Ser Asp Val Leu Leu Ala Gly Thr
            180                 185                 190

Ala Lys

<210> SEQ ID NO 7
<211> LENGTH: 104
<212> TYPE: PRT
<213> ORGANISM: Salmonid alphavirus subtype 3

<400> SEQUENCE: 7

Glu His Gln Val Thr Glu Lys Phe Thr Arg Glu Arg Ser Lys Gly His
 1               5                  10                  15

His Leu Ser Asp Leu Thr Lys Lys Cys Thr Arg Phe Ser Thr Thr Pro
            20                  25                  30

Lys Lys Ser Ala Pro Tyr Leu Val Asp Val Tyr Asp Ala Leu Pro Ile
        35                  40                  45

Ser Val Glu Ile Ser Thr Val Val Thr Cys Asn Asp Asn Gln Cys Thr
 50                  55                  60

Val Arg Val Ser Pro Gly Thr Thr Val Lys Phe Asp Lys Lys Cys Lys
65                   70                  75                  80

Ser Ala Ala Gln Ala Thr Val Thr Phe Thr Ser Asp Ser Gln Thr Phe
```

```
                85                  90                  95
Thr Cys Glu Glu Pro Val Leu Thr
            100

<210> SEQ ID NO 8
<211> LENGTH: 83
<212> TYPE: PRT
<213> ORGANISM: Salmonid alphavirus subtype 3

<400> SEQUENCE: 8

Pro Lys Lys Ser Ala Pro Tyr Leu Val Asp Val Tyr Asp Ala Leu Pro
1               5                   10                  15

Ile Ser Val Glu Ile Ser Thr Val Thr Cys Asn Asp Asn Gln Cys
            20                  25                  30

Thr Val Arg Val Ser Pro Gly Thr Thr Val Lys Phe Asp Lys Lys Cys
        35                  40                  45

Lys Ser Ala Ala Gln Ala Thr Val Thr Phe Thr Ser Asp Ser Gln Thr
    50                  55                  60

Phe Thr Cys Glu Glu Pro Val Leu Thr Ala Ala Ser Ile Thr Gln Gly
65                  70                  75                  80

Lys Pro His

<210> SEQ ID NO 9
<211> LENGTH: 20
<212> TYPE: DNA
<213> ORGANISM: Artificial
<220> FEATURE:
<223> OTHER INFORMATION: PCR primer

<400> SEQUENCE: 9
ttgacgtgta cgacgctctg                                              20

<210> SEQ ID NO 10
<211> LENGTH: 22
<212> TYPE: DNA
<213> ORGANISM: Artificial
<220> FEATURE:
<223> OTHER INFORMATION: PCR primer

<400> SEQUENCE: 10
aaccggctcc tcacacgtaa ac                                           22

<210> SEQ ID NO 11
<211> LENGTH: 31
<212> TYPE: DNA
<213> ORGANISM: Artificial
<220> FEATURE:
<223> OTHER INFORMATION: PCR primer

<400> SEQUENCE: 11
ccgcgcgagc ccctggtatg caacacagtg c                                 31

<210> SEQ ID NO 12
<211> LENGTH: 33
<212> TYPE: DNA
<213> ORGANISM: Artificial
<220> FEATURE:
<223> OTHER INFORMATION: PCR primer

<400> SEQUENCE: 12
ataccagggg ctcgcgcctc gagaccctac ttg                               33
```

<210> SEQ ID NO 13
<211> LENGTH: 33
<212> TYPE: DNA
<213> ORGANISM: Artificial
<220> FEATURE:
<223> OTHER INFORMATION: PCR primer

<400> SEQUENCE: 13
gatgccataa gcttgacacg cgctccggcc ctc                      33

<210> SEQ ID NO 14
<211> LENGTH: 28
<212> TYPE: DNA
<213> ORGANISM: Artificial
<220> FEATURE:
<223> OTHER INFORMATION: PCR primer

<400> SEQUENCE: 14
cgtcactttc accagcgact cccagacg                            28

<210> SEQ ID NO 15
<211> LENGTH: 29
<212> TYPE: DNA
<213> ORGANISM: Artificial
<220> FEATURE:
<223> OTHER INFORMATION: PCR primer

<400> SEQUENCE: 15
ggatccattc ggatgtggcg ttgctatgg                           29

<210> SEQ ID NO 16
<211> LENGTH: 23
<212> TYPE: DNA
<213> ORGANISM: Artificial
<220> FEATURE:
<223> OTHER INFORMATION: PCR primer

<400> SEQUENCE: 16
catatgatcc tggccagctg ccc                                 23

<210> SEQ ID NO 17
<211> LENGTH: 28
<212> TYPE: DNA
<213> ORGANISM: Artificial
<220> FEATURE:
<223> OTHER INFORMATION: PCR primer

<400> SEQUENCE: 17
aatacatatg gaacatcaag taacggag                            28

<210> SEQ ID NO 18
<211> LENGTH: 30
<212> TYPE: DNA
<213> ORGANISM: Artificial
<220> FEATURE:
<223> OTHER INFORMATION: PCR primer

<400> SEQUENCE: 18
aatacatatg gacctgacca agaagtgcac                          30

<210> SEQ ID NO 19
<211> LENGTH: 28
<212> TYPE: DNA
<213> ORGANISM: Artificial
<220> FEATURE:
<223> OTHER INFORMATION: PCR primer

<400> SEQUENCE: 19
aatacatatg ctcgttgacg tgtacgac                                              28

<210> SEQ ID NO 20
<211> LENGTH: 30
<212> TYPE: DNA
<213> ORGANISM: Artificial
<220> FEATURE:
<223> OTHER INFORMATION: PCR primer

<400> SEQUENCE: 20
tatatccatg gcttcgcggt accggccagc                                            30

<210> SEQ ID NO 21
<211> LENGTH: 28
<212> TYPE: DNA
<213> ORGANISM: Artificial
<220> FEATURE:
<223> OTHER INFORMATION: PCR primer

<400> SEQUENCE: 21
tatccatggg atcgacggca gcggggcg                                              28

<210> SEQ ID NO 22
<211> LENGTH: 28
<212> TYPE: DNA
<213> ORGANISM: Artificial
<220> FEATURE:
<223> OTHER INFORMATION: PCR primer

<400> SEQUENCE: 22
tatccatggg atcctcgcct tcacttcc                                              28

<210> SEQ ID NO 23
<211> LENGTH: 26
<212> TYPE: DNA
<213> ORGANISM: Artificial
<220> FEATURE:
<223> OTHER INFORMATION: PCR primer

<400> SEQUENCE: 23
tatccatggg tgcggcttgc cctggg                                                26

<210> SEQ ID NO 24
<211> LENGTH: 27
<212> TYPE: DNA
<213> ORGANISM: Artificial
<220> FEATURE:
<223> OTHER INFORMATION: PCR primer

<400> SEQUENCE: 24
tatccatggg ggagtcgctg gtaaagg                                               27

<210> SEQ ID NO 25
<211> LENGTH: 19
<212> TYPE: DNA
<213> ORGANISM: Artificial
<220> FEATURE:
<223> OTHER INFORMATION: PCR primer

<400> SEQUENCE: 25
aatacgactc actataggg                                                        19

<210> SEQ ID NO 26
<211> LENGTH: 19

```
<212> TYPE: DNA
<213> ORGANISM: Artificial
<220> FEATURE:
<223> OTHER INFORMATION: PCR primer

<400> SEQUENCE: 26
gctagttatt gctcagcgg                                              19

<210> SEQ ID NO 27
<211> LENGTH: 34
<212> TYPE: DNA
<213> ORGANISM: Artificial
<220> FEATURE:
<223> OTHER INFORMATION: PCR primer

<400> SEQUENCE: 27
gtatgcccat ggaacgtcgt tttacaacgt cgtg                             34

<210> SEQ ID NO 28
<211> LENGTH: 37
<212> TYPE: DNA
<213> ORGANISM: Artificial
<220> FEATURE:
<223> OTHER INFORMATION: PCR primer

<400> SEQUENCE: 28
gtctcgctcg agttattttt gacaccagac caactgg                          37
```